(12) United States Patent
Mayer et al.

(10) Patent No.: US 12,037,265 B2
(45) Date of Patent: Jul. 16, 2024

(54) PROCESS FOR CONTROLLED ADSORPTION AND DESORPTION OF PHOSPHATE FROM LIQUIDS USING PHOSPHATE-SELECTIVE PROTEINS

(71) Applicant: Marquette University, Milwaukee, WI (US)

(72) Inventors: Brooke Mayer, Milwaukee, WI (US); Kaushik Venkiteshwaran, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 788 days.

(21) Appl. No.: 17/153,471

(22) Filed: Jan. 20, 2021

(65) Prior Publication Data

US 2021/0147259 A1 May 20, 2021

Related U.S. Application Data

(63) Continuation-in-part of application No. PCT/US2019/042652, filed on Jul. 19, 2019.
(Continued)

(51) Int. Cl.
*C02F 1/28* (2023.01)
*B01J 20/34* (2006.01)
(Continued)

(52) U.S. Cl.
CPC .......... *C02F 1/286* (2013.01); *B01J 20/3475* (2013.01); *C12Q 1/00* (2013.01); *G01N 30/00* (2013.01);
(Continued)

(58) Field of Classification Search
CPC ............... C02F 1/286; C02F 2101/105; C02F 2103/34; C02F 2303/16; C02F 2103/007; C02F 2209/06; B01J 20/3475; B01J 20/24; B01J 20/3219; B01J 20/3274; B01J 20/3425; B01J 20/3212; C12Q 1/00; G01N 30/00; G01N 30/06; G01N 30/88;
(Continued)

(56) References Cited

U.S. PATENT DOCUMENTS

| 5,898,069 A | 4/1999 | Webb |
| 2005/0156136 A1 | 7/2005 | SenGupta |

FOREIGN PATENT DOCUMENTS

| JP | 2000317304 A | * 11/2000 |
| WO | 2004035792 A1 | 4/2004 |
| WO | 2013175423 A1 | 11/2013 |

OTHER PUBLICATIONS

Kuroda et al. English translation of JP2000317304A (Year: 2000).*
(Continued)

*Primary Examiner* — Soren Harward
*Assistant Examiner* — Naghmeh Nina Moazzami
(74) *Attorney, Agent, or Firm* — Quarles & Brady LLP

(57) ABSTRACT

The present invention provides systems and methods for concentrating and recovering phosphate from samples. The method comprises using immobilized PBP for binding phosphate and a desorption solution having a pH of 11 or greater to recover phosphate from a sample when the phosphate is found at very low detection levels. Further systems and method for removing arsenate for water sources is also provided.

20 Claims, 12 Drawing Sheets

Specification includes a Sequence Listing.

Related U.S. Application Data

(60) Provisional application No. 62/701,235, filed on Jul. 20, 2018.

(51) Int. Cl.
    | | |
    |---|---|
    | C02F 101/10 | (2006.01) |
    | C02F 103/34 | (2006.01) |
    | C12Q 1/00 | (2006.01) |
    | G01N 30/00 | (2006.01) |
    | G01N 30/06 | (2006.01) |
    | G01N 30/88 | (2006.01) |

(52) U.S. Cl.
    CPC ........ *G01N 30/06* (2013.01); *C02F 2101/105* (2013.01); *C02F 2103/34* (2013.01); *C02F 2303/16* (2013.01); *G01N 30/88* (2013.01)

(58) Field of Classification Search
    CPC .... G01N 33/5308; Y02A 40/20; C05B 17/00; C05F 7/00; C07K 14/195; C07K 14/245; C07K 14/25; C07K 17/14
    See application file for complete search history.

(56) References Cited

OTHER PUBLICATIONS

Acelas, N.Y., et al., 2015. Selective removal of phosphate from wastewater using hydrated metal oxides dispersed within anionic exchange media. Chemosphere 119, 1353-1360.
Awual, M.R., et al., 2011. Removal of trace arsenic(V) and phosphate from water by a highly selective ligand exchange adsorbent. J. Environ. Sci. 23, 1947-1954.
Blaney, L.M., et al., 2007. Hybrid anion exchanger for trace phosphate removal from water and wastewater. Water Res. 41, 1603-1613.
Blank, L.M., 2012. The cell and P: From cellular function to biotechnological application. Curr. Opin. Biotechnol. 23, 846-851.
Brune, M., et al., 1994. Direct, Real-Time Measurement of Rapid Inorganic Phosphate Release Using a Novel Fluorescent Probe and Its Application to Actomyosin Subfragment 1 ATPase. Biochemistry 33, 8262-8271.
Brune, M., et al., 1998. Mechanism of inorganic phosphate interaction with phosphate binding protein from *Escherichia coli*. Biochemistry 37, 10370-10380.
Calderon, R.L., et al., 1999. Excretion of arsenic in urine as a function of exposure to arsenic in drinking water. Environ. Health Perspect. 107, 663-7.
Carvalho, L.H.M., et al., 1998. An improved molybdenum blue method for simultaneous determination of inorganic phosphate and arsenate. Ecotoxicol. Environ. Restor. 1, 13-19.
Chen, W. et al. "Cell-surface display of heterologous proteins: From high-throughput screening to environmental applications." Biotechnology and bioengineering 79.5 (2002): 496-503.
Choi SS, et al. Biological removal of phosphate at low concentrations using recombinant *Escherichia coli* expressing phosphate-binding protein in periplasmic space. Appl Biochem Biotechnol. 2013;171:1170-1177. doi:10.1007/s12010-013-0187-1.
Cordell, D. et al. "Life's bottleneck: sustaining the world's phosphorus for a food secure future." Annual Review of Environment and Resources 39 (2014): 161-188.
Cordell, D. et al. The Story of Phosphorus: Global Food Security and Food for Thought. Glob. Environ. Chang. 2009, 19 (2), 292-305.
Cortinas, I., et al., 2006. Anaerobic biotransformation of roxarsone and related N-substituted phenylarsonic acids. Environ. Sci. Technol. 40, 2951-2957.
Cullen, W.R., et al., 1989. Arsenic Speciation in the Environment. Chem. Rev. 89, 713-764.
Elias, M., et al., 2012. The molecular basis of phosphate discrimination in arsenate-rich environments. Nature 491, 134-137.
Georgiou, G., et al. "Display of heterologous proteins on the surface of microorganisms: from the screening of combinatorial libraries to live recombinant vaccines." Nature biotechnology 15.1 (1997): 29-34.
Gruber, M. F. "Environmental Phosphorus Recovery Based on Molecular Bioscavengers." Technical University of Denmark. Doctoral Thesis. (2016).
Hartley, T.N., et al., 2013. Historical arsenic contamination of soil due to long-term phosphate fertiliser applications. Environ. Pollut. 180, 259-264.
Hussein, F. B., et al. "Cell surface-expression of the phosphate-binding protein PstS: System development, characterization, and evaluation for phosphorus removal and recovery." Journal of Environmental Sciences 92 (2020): 129-140.
International Searching Authority. International Search Report and Written Opinion for application PCT/US2019/042652. Mailed on Nov. 5, 2019. 11 pages.
Jayasumana, C., et al., 2015. Phosphate fertilizer is a main source of arsenic in areas affected with chronic kidney disease of unknown etiology in Sri Lanka. Springerplus 4, 1-8.
Kumar, P.S., et al., 2019. Adsorption as a technology to achieve ultra-low concentrations of phosphate: Research gaps and economic analysis. Water Res. X.
Kuroda A, et al. Evaluation of phosphate removal from water by immobilized phosphate-binding protein PstS. J Biosci Bioeng. 2000;90(6):688-690.
Li Q, et al. Improved phosphate biosorption by bacterial surface display of phosphate-binding protein utilizing ice nucleation protein. FEMS Microbiol Lett. 2009;299(1):44-52.
Li, L. et al. "Functional display of foreign protein on surface of *Escherichia coli* using N-terminal domain of ice nucleation protein." Biotechnology and bioengineering 85.2 (2004): 214-221.
Luecke, H., et al., 1990. High specificity of a phosphate transport protein determined by hydrogen bonds. Nature 347, 402-406.
Mayer, B.K., et al., 2013. Innovative strategies to achieve low total phosphorus concentrations in high water flows. Crit. Rev. Environ. Sci. Technol. 43, 409-441.
Mayer, B.K., et al., 2016. Total Value of Phosphorus Recovery. Environ. Sci. Technol. 50, 6606-6620.
Mortvedt, J.J., 1995. Heavy metal contaminants in inorganic and organic fertilizers. Fertil. Res. 43, 55-61.
Nicomel, N.R., et al., 2015. Technologies for Arsenic Removal from Water: Current Status and Future Perspectives. Int. J. Environ. Res. Public Health 13, ijerph13010062.
Pan, B., et al., 2009. Development of polymer-based nanosized hydrated ferric oxides (HFOs) for enhanced phosphate removal from waste effluents. Water Res. 43, 4421-4429.
Pintor, A.M.A., et al., 2020. Complexation mechanisms in arsenic and phosphorus adsorption onto iron-coated cork granulates. J. Environ. Chem. Eng. 8, 104184.
Rittmann, B.E., et al., 2011. Capturing the lost phosphorus. Chemosphere 84, 846e853.
Ronteltap, M., et al., 2007. The behaviour of pharmaceuticals and heavy metals during struvite precipitation in urine. Water Res. 41, 1859-1868.
Santos-Beneit, F., et al., 2008. Phosphate-dependent regulation of the low- and high-affinity transport systems in the model actinomycete Streptomyces coelicolor. Microbiology 154, 2356-2370.
Schroder, J. J., et al. Sustainable use of phosphorus: EU tender Env. B1/ETU/2009/0025. No. 357. Plant Research International, 2010.
Solscheid, C., et al, 2015. Development of a Reagentless Biosensor for Inorganic Phosphate, Applicable over a Wide Concentration Range. Biochemistry 54, 5054-5062.
USEPA, 2016. Office of Water Definition and Procedure for the Determination of the Method Detection Limit, Revision 2. United States Environ. Prot. Agency, Off. Water. URL: www.epa.gov/cwa-methods/procedures-detection-and-quantitation-documents. 8 pages.
USEPA. Advanced Wastewater Treatment to Achieve Low Concentration of Phosphorus. United States Environ. Prot. Agency, Off. Water Watersheds Reg. 2007, 73.
Uysal, A., et al., 2010. The determination of fertilizer quality of the formed struvite from effluent of a sewage sludge anaerobic digester. J. Hazard. Mater. 181, 248-254.

(56) References Cited

OTHER PUBLICATIONS

Venkiteshwaran, K., et al. "Immobilized phosphate-binding protein can effectively discriminate against arsenate during phosphate adsorption and recovery." Water Environment Research (2020).

Venkiteshwaran, K., et al. "Kinetics, affinity, thermodynamics, and selectivity of phosphate removal using immobilized phosphate-binding proteins." Environmental Science & Technology 54.17 (2020): 10885-10894.

Venkiteshwaran, K., et al. "Phosphate removal and recovery using immobilized phosphate binding proteins." Water research X 1 (2018): 100003.

Yang, C.H., et al., 2020. Covalent organic framework EB-COF:Br as adsorbent for phosphorus (V) or arsenic (V) removal from nearly neutral waters. Chemosphere 253, 126736.

Yang, Y., et al. 2016. High affinity phosphate binding protein (PBP) for phosphorus recovery: Proof of concept using recombinant *Escherichia coli*. FEMS Microbiol. Letters. 363(20), 1-6. DOI: 10.1093/femsle/fnw240.

Yang, Y., et al. 2017. Biological phosphorus recovery: Current progress and future needs. Water Environ. Res. 89(9), 2122-2125.

You, X., et al., 2016. Phosphate removal from aqueous solution using a hybrid impregnated polymeric sorbent containing hydrated ferric oxide (HFO). J. Chem. Technol. Biotechnol. 91, 693-704.

Zhu, N., et al., 2016. Adsorption of arsenic, phosphorus and chromium by bismuth impregnated biochar: Adsorption mechanism and depleted adsorbent utilization. Chemosphere 164, 32-40.

Gomez-Caminero, et al., Environmental Health Criteria 224, Arsenic and Arsenic Compounds, Second edition, 2001, Sec. 12; 12 pages, World Health Organization, Geneva, Switzerland; downloaded at https://www.inchem.org/documents/ehc/ehc/ehc224.htm#1.0.

\* cited by examiner

PROCESS FOR CONTROLLED ADSORPTION AND DESORPTION OF PHOSPHATE FROM LIQUIDS USING PHOSPHATE-SELECTIVE PROTEINS

CROSS-REFERENCE TO RELATED APPLICATIONS

This application is a continuation-in-part of International Application No. PCT/US2019/042652 filed on Jul. 19, 2019, which claims priority to U.S. Provisional Application No. 62/701,235 filed on Jul. 20, 2018, the contents of which are incorporated by reference in their entireties.

STATEMENT REGARDING FEDERALLY SPONSORED RESEARCH

This invention was made with government support under 1554511 awarded by the National Science Foundation. The government has certain rights to the invention.

SEQUENCE LISTING

A Sequence Listing accompanies this application and is submitted as an ASCII text file of the sequence listing named "630024_00205_ST25.txt" which is 29.9 KB in size and was created on Jan. 20, 2021. The sequence listing is electronically submitted via EFS-Web with the application and is incorporated herein by reference in its entirety.

BACKGROUND OF THE INVENTION

The field of the invention is related to the ability to selectively adsorb and desorb phosphate from a liquid solution under controlled conditions. This method can be used to 1) facilitate measurement of ultra-low phosphate concentrations and 2) to recover phosphate for reuse.

Phosphate ($P_i$) is an essential nutrient for global food supply and is a non-renewable and increasingly expensive resource. (Cordell et al., 2009; Cordell and White, 2014; Mayer et al., 2016; Rittmann et al., 2011). At the same time, the presence of $P_i$ in fresh water sources can cause severe algal blooms, leading to ecological and economic losses. (Schröder et al., 2010; USEPA, 2007). In light of this, a system which can effectively remove $P_i$ down to ultra-low levels (<100 µg/L) and release $P_i$ under controlled conditions for reuse as fertilizer is essential for attaining an environmentally sustainable and economically viable solution. (Mayer et al., 2013; Rittmann et al., 2011). Additionally, improved analytical quantification techniques to accurately measure ultra-low levels of $P_i$ are important for monitoring its presence in aquatic matrices.

There have been numerous approaches developed and tested to try and achieve ultra-low levels of $P_i$ detection and removal/recovery. Prior removal methods include physical-chemical (e.g., coagulation using iron followed by sedimentation, filtration using iron-based media) as well as biological (e.g., enhanced biological phosphorus removal). To more selectively, and reversibly, recover phosphorus from heterogeneous liquids, one approach that has attracted increasing interest is ion exchange. Synthetic beads (also referred as resins) can be designed to more selectively remove $P_i$. One example is LayneRT resin (a commercialized product originally developed at Lehigh University). However the current methods still lack the ability to bind ultra-low levels of $P_i$ or the specificity to produce a purer product (e.g. reduce non-specific binding with arsenate).

There is a need for highly sensitive and specific methods of removing and concentrating $P_i$ from a liquid sample, particularly when present at initially low levels, to facilitate improved recovery and quantification.

SUMMARY OF THE INVENTION

The present invention provides methods, kits and systems for concentrating and recovering phosphate ($P_i$) from a sample. The methods, kits and systems of the present invention may facilitate measurement of ultra-low concentrations and recovery of $P_i$ for reuse.

In one aspect, the present disclosure provides a method of concentrating and recovering $P_i$ from a sample, the method comprising: (a) exposing a liquid sample to immobilized $P_i$ binding protein (PBP) for a sufficient amount of time to bind phosphate to the immobilized PBP within the sample; and (b) desorbing the $P_i$ from the immobilized PBP by contacting the immobilized PBP with a desorption solution having a pH of 11 or greater (e.g., 11.4), preferably a pH of 12 or greater, wherein the $P_i$ is concentrated with the desorption solution. In some aspects, step (a) further comprises a wash step with a washing solution at a neutral pH (preferably between pH 6.8-7.5) to remove non-specific binding of other ions in the sample.

In some aspects, the method further comprises: (c) reusing the immobilized PBP by (i) washing the immobilized PBP with a washing solution at a neutral pH between pH 6.8-7.5, and (ii) re-exposing the immobilized PBP with a second sample, (iii) desorbing the $P_i$ from the immobilized PBP by exposing the immobilized PBP to desorption solution of pH of 11 or higher, preferably a pH of 12 or higher, and (iv) recovering the $P_i$ in the desorption solution.

In another aspect, the present disclosure provides a method of concentrating low levels of $P_i$ in a sample, the method comprising: (a) exposing a liquid sample to immobilized phosphate binding protein (PBP) for a sufficient amount of time to bind phosphate to the immobilized PBP within the sample; (b) desorbing the phosphate from the immobilized PBP by contacting the immobilized PBP with a desorption solution having a pH of 11 or higher, preferably a pH of 12 or greater wherein the volume of the desportion solution is at least 2 to 10 times smaller than the starting sample volume and the phosphate is concentrated to a detectable level.

In a further aspect, the disclosure provides a kit for improved detection or quantification of low levels of phosphate in a liquid sample or concentrating phosphate from a liquid sample, the kit comprising (a) immobilized PBP; (b) a desorption solution having a pH of 11 or higher, preferably a pH of 12 or greater, and (c) instructions for adsorbing and desorbing the phosphate from the immobilized PBP.

In yet another aspect, the disclosure provides a method of removing arsenate (As(V)) from a water source, the method comprising: (a) exposing a liquid sample to immobilized phosphate binding protein (PBP) for a sufficient amount of time to bind As(V) to the immobilized PBP within the sample; (b) and removing the As(V) bound immobilized PBP from the sample. In some aspects, the method further comprising (b) contacting the immobilized PBP with a desorption solution having a pH of 11 or greater or a desorption solution comprising excess $P_i$ to desorbing the As(V) from the immobilized PBP. In some examples, the water source has low or undetectable levels of $P_i$.

In another aspect, the disclosure provides a system and compositions for removing As(V) from a water source, the system or composition comprising immobilized PBP in a sufficient amount to bind to As(V) in a water source.

The foregoing and other aspects and advantages of the invention will appear from the following description. In the description, reference is made to the accompanying drawings which form a part hereof, and in which there are shown, by way of illustration, preferred embodiments of the invention. Such embodiments do not necessarily represent the full scope of the invention, however, and reference is made therefore to the claims and herein for interpreting the scope of the invention.

DETAILED DESCRIPTION OF THE INVENTION

Figure 1A:
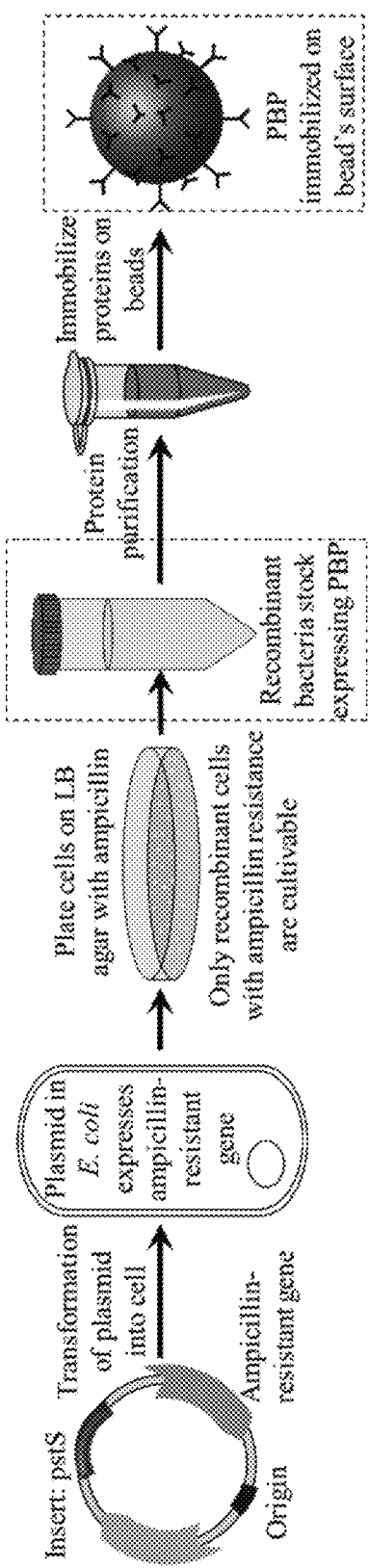
FIG. 1A is a cartoon representation of the method of the current invention using the engineered systems (both recombinant bacteria expressing the phosphate binding protein [PBP] and the PBP immobilized on a bead surface, as signified by the dotted lines).

The present invention provides methods of removing, concentrating and purifying $P_i$ from a liquid sample, specifically ultra-low concentrations of $P_i$, to facilitate downstream phosphorus quantification or reuse.

The present invention provides immobilized PBP in engineered systems (preferably either attached to a surface, e.g., a plastic bead, or expressed on the surface of bacterial cells) to recover $P_i$ from liquids, even in conditions in which the $P_i$ is found in ultra-low levels (e.g. levels below 100 μg/L, preferably below 50 μg/L, and including levels below 20 μg/L).

The present invention provides an improved process to selectively adsorb and desorb phosphorus from liquids including, but not limited to, for example, environmental waters and wastewaters. By removing the phosphorus, the environmental degradation caused by excess phosphorus in water is alleviated. The recovered phosphorus can be reused for beneficial purposes, e.g., to supplement depleting global supplies of the mineral phosphorus used to produce agricultural fertilizer.

In some embodiments, the methods of the present invention provide selective adsorption and recovery of phosphorus that can be used for improved quantification of phosphorus in environmental water samples. Current standard methods (colorimetric or ion chromatograph) can reliably detect $P_i$ at >50 ug/L. Standard colorimetric methods can detect $P_i$ from 20-50 ug/L; however, error in measurement is more than 10% and reliability is low. Ion chromatographs require an anion exchange solid phase extraction (SPE) cartridge to measure phosphorus below 50 μg/L. However, there are no known SPE cartridges available to specifically concentrate phosphorus. Phosphorus-induced eutrophication has been shown to occur at concentrations below 50 μg/L. The lack of reliable detection methods between ~0 to 50 μg/L hinders identification of issues and implementation of remedial measures that could be applied before phosphorus reaches critical levels in environmental waters. The method of the present invention provides methods to improve $P_i$ quantification at ultra-low levels by selectively adsorbing $P_i$ from water samples (<50 μg/L) and subsequently desorbing phosphorus in lower volumes (concentrated at >100 μg/L), which can be quantified using conventional methods.

The methods described herein use PBPs to capture and release $P_i$ under controlled conditions that allow for the unexpectedly low capture and concentration of $P_i$. PBP is naturally expressed in some bacteria under low $P_i$ conditions. Bacteria express the protein in their periplasmic space as part of a high-affinity $P_i$-specific transporter system. The PBP selectively binds inorganic phosphorus (i.e., $P_i$) in a deep cleft using 12 hydrogen bonds. The $P_i$ is then transported into the cell for use in the cell's metabolic machinery, e.g., to build DNA or to store energy (ATP). The PBP protein may contain a tag that allows for it to be attached to the surface or inert material (e.g., bead or membrane) for use in the present invention.

Suitable PBP proteins are known in the art and are not limited to the examples described herein. PBP is a multi-species ABC transporter protein found in several species of proteobacteria (NCBI Reference Sequence: WP_000867146.1) and is highly conserved between bacteria. PBP features 7 different amino acid residues that form 12 strong hydrogen bonds with $P_i$, as illustrated in Venkiteshwaran et al. (2018), incorporated by reference in its entirety.

Any suitable PBP that binds to $P_i$ can be used in the practice of this invention. Suitable PBP include, for example, wildtype and modified PBP obtained from any suitable bacterial strain, which maintain their ability to bind $P_i$. Suitable PBP examples include, for example, *E. coli* or *Shigella flexneri*, among others. While the PBP protein disclosed in the Examples was derived from *E. coli* K-12 strain, many other PBP proteins may be used in the present invention. PBP is a highly conserved protein. According to UniProt, over 100 different microorganisms have PBP proteins with an identical amino acid sequence (100% identity) to that found in *E. coli* K-12 strain (SEQ ID NO: 1). These microorganisms include many other strains of *E. coli*, as well as several species of *Shigella*. Notably, among these proteins, the PBP of *Shigella flexneri* 301 strain is the only other PBP protein that has been manually curated and reviewed (SEQ ID NO: 7). Additionally, many microorganisms have PBP proteins that are nearly identical to that of *E. coli* K-12 strain (UniProt lists over 350 with greater than 90% identity). Closely related PBP proteins include, without limitation, those of *E. coli* UMEA 3200-1 (SEQ ID NO: 9, 99.4% identity), *Shigella boydii* ATCC 9905 (SEQ ID NO: 10, 99.7% identity), and *Trichuris trichiura* (SEQ ID NO: 11, 98.8% identity). For example, PBP from the *E. coli* K-12 strain, substrain MG1655 (NCBI Reference Sequence: NP_418184.1; GenBank: AYG21454.1; UniProtKB—P0AG82 (SEQ ID NO:1), including the PBP without the signal sequence (e.g., SEQ ID NO:2, SEQ ID NO:6) or modified *E. coli* PBP (e.g., SEQ ID NO:4, SEQ ID NO:5), or the PBP of *Shingella* (SEQ ID NO:7) or sequence that have at least 80% identity to the PBP of any one of SEQ ID NO:1-7 can be used in the practice of the invention. Suitable PBP proteins include, for example, PBP proteins that share substantial identity to the polypeptide found in any one of SEQ ID NO:1-7, including modified proteins that maintain the ability to bind $P_i$. SEQ ID NO: 2 is PBP amino acid sequence from *E. coli* K-12 strain, substrain MG1655 (NCB Reference Sequence: NP_418184.1; GenBank: AYG21454.1; UniProtKB-P0AG82) with the signal peptide removed and replaced with start codon methionine (M). SEQ ID NO:3 is gene sequence associated with the PBP from *E. coli* K-12 strain, substrain MG1655 (GenBank: CP032667.1.). SEQ ID NO:4 is the amino acid sequence PBP sequence PBP A197C from *E. coli* K-12 strain (addgene id: pET22b_PstS_1) with the signal peptide removed and replaced with methionine (M), and alanine (A) in position 197 replaced with cysteine (C). SEQ ID NO:5 is the gene sequence or the associated PBP of SEQ ID NO:4. SEQ ID NO:6 is PBP without the signal sequence from in *E. coli* K-12 strain.

In some embodiments, the PBP have at least 75% sequence identity to any one of SEQ ID NO:1-7, alternatively at least 80% sequence identity, alternatively at least 85% sequence identity, alternatively at least 90% sequence identity, alternatively at least 95% sequence identity, alternatively at least 97% sequence identity, alternatively at least 98% sequence identity, alternatively at least 99% sequence identity, alternatively at least 100% sequence identity to any one of SEQ ID NO: 1-7. The term "substantial identity" of protein sequences means that a protein comprises a sequence that has at least 75% sequence identity to the polypeptide of interest described herein. Alternatively, percent identity can be any integer from 75% to 100%. More preferred embodiments include at least: 75%, 80%, 85%, 86%, 87%, 88%, 89%, 90%, 91%, 92%, 93%, 94%, 95%, 96%, 97%, 98% or 99% compared to a reference sequence using the programs known in the art; for example BLAST using standard parameters. These values can be appropriately adjusted to determine corresponding identity of proteins encoded by two nucleotide sequences by taking into account codon degeneracy, amino acid similarity, reading frame positioning and the like.

Additionally, the PBP protein or modified protein may further comprise a tag that allows for ease of mass producing the PBP protein for use in the methods described herein. Suitable tags are known in the art and include but are not limited to, for example, epitope tags which are known in the art and include, but are not limited to, 6-Histidine (His, HHHHHH), cMyc (EQKLISEEDL), FLAG (DYKDDDDK), V5-tag (GKPIPNPLLGLDST), HA-tag (YPYDVPDYA), NE-tag (TKENPRSNQEESYDDNES), S-tag (KETAAAKFERQHMDS), Ty tag (EVHTNQDPLD), among others. Epitope tags are commonly used as a purification tag. A purification tag is an agent that allows isolation of the polypeptide from other non-specific proteins.

The wildtype *E. coli* K-12 PBP has 346 amino acid bases (SEQ ID NO:1). The complete genome sequence of *E. coli* K-12 strain, substrain MG1655 can be found using the reference ID GenBank: CP032667.1 where the protein gene sequence is located between base pairs 4611542 to 4612582. The length of the PBP gene is 1041 nucleotides. Expressed wild type PBP amino acid sequence from the *E. coli* K-12 strain, substrain MG1655 (NCBI Reference Sequence: NP_418184.1; GenBank: AYG21454.1; UniProtKB-P0AG82) is found in SEQ ID NO:1 (346 amino acids with a 22 aa signal peptide at the beginning). Suitable, for producing large quantities Other PBP sequences This sequence is similar to the reference sequence for multispecies PBP ABC transporter in the database (NCBI Reference Sequence: WP_000867146.1).

In the newly developed system, PBP is used to selectively capture $P_i$ as a reversible ligand such that the $P_i$ can be released back into solution in a controlled fashion at a high pH (e.g. a pH of about 12 or greater). The $P_i$ is released back into solution in a concentrated and pure form.

The high specificity of the use of PBP allows for the recovered and concentrated $P_i$ isolated by the current invention to be of high purity, e.g. at least 50% $P_i$, more preferably at least 75% $P_i$, alternatively at least 80% $P_i$, alternatively at least 85% $P_i$, alternatively at least 90% $P_i$, alternatively at least 95% $P_i$. In a preferred embodiment, the purity is at least about 90%.

In one embodiment, the present invention provides a method of concentrating and recovering $P_i$ from a sample, the method comprising: (a) exposing a liquid sample to immobilized PBP for a sufficient amount of time to bind $P_i$ to the immobilized PBP within the sample; and an optional wash step with a washing solution at a neutral pH (preferably between pH 6.8-7.5) to remove non-specific binding of other ions in the water, and (b) desorbing the $P_i$ from the immobilized PBP by contacting the immobilized PBP with a desorption solution having a pH of 11 or greater, preferably a pH of 11.4 or greater, more preferably having a pH of 12 or greater, wherein the $P_i$ is concentrated with the desorption solution. The volume of the desorption solution can be 2 to 10 times smaller than the raw liquid sample. In some embodiments, the desorption solution containing the $P_i$ is altered to a neutral pH by the addition of an acid (for example, but not limited to, HCl, citric acid, etc.). Once neutralized, the desorption solution containing the $P_i$ may be used for quantification of $P_i$ or recovered for reuse applications, e.g., as struvite. Suitable desorption solutions are able to be determined by one skilled in the art, and include any solution able to have a pH of 11 or greater, preferably a pH of 11.4 or greater, more preferably having a pH of 12 or greater (e.g., pH of 12.5). Suitable desorption solutions include any buffer with a pH greater than 11, preferably greater than 12, including, but not limited to, water, Tris buffer, among others. For example, as described in the Examples below, some examples of suitable desorption solutions include deionized water, Milli-Q water, 10 mM Tris+1 mM $MgCl_2$ buffer at a pH greater than 11, preferably greater than 12, for example, a pH of 12.5. As disclosed in the Examples, the higher the pH above 11, the more effective the desorption is. For example, a desorption solution of a pH of 11.4 allows for desorption of about 60% of the $P_i$, while a desorption solution of pH of 12 allows for desorption of over 80%, preferably over 90% and up to 100% of the desportion of the $P_i$ from the PBP as demonstrated in the examples. As denoted in the examples, a desorption solution at a pH of 12.5 was able to desorb 100% of the $P_i$. Again, suitable desorption solutions with a pH greated than 11, preferably greater than 12 can be determined by one skilled in the art and are not limited by the Examples and embodiments provided herein.

In some embodiments, the method further comprises (c) quantifying the $P_i$ within the desorption solution of step (b). Suitable methods of detection or quantification are known in the art and include, but are not limited to, for example, detected by colorimetric methods or ion chromatography.

The term "immobilized PBP" as referred to herein refers to PBP attached or complexed to a surface or inert material, for example, a bead, membrane or bacteria. In some methods, the PBP is expressed on the surface of bacteria.

In one embodiment, the PBP is immobilized on bacteria. By "immobilized on bacteria" as used herein, the PBP is expressed on the surface of the bacterial cell. Suitable methods of expressing a protein on the surface of a cell are known in the art, as described in, for example, Chen and Georgiou, 2002, Georgiou et al., 1997; Li et al., 2004, the contents of which are incorporated by reference. Any suitable method to surface display the PBP on the surface of the bacteria are contemplated, including, but not limited to, for example, cell surface display of heterologous PBP on the cell's outer membrane using the N-terminal domain of the ice nucleation protein as its anchoring motif as described in the Examples below. Briefly, the bacteria are transformed using the recombinant plasmid containing the relevant ice nucleation protein and PBP into *E. coli* cells using standard procedures.

A benefit of the present methods and systems is the ability to re-use the immobilized PBP for additional adsorption/desorption cycles. In some embodiments, the method further comprises: d) reusing the immobilized PBP by (i) washing the immobilized PBP with a washing solution at a neutral pH (preferably between pH 6.8-7.5), (ii) re-exposing the immobilized PBP with a second sample, (iii) desorbing the $P_i$ from the immobilized PBP by exposing the immobilized PBP to desorption solution of pH of 12 or higher, and (iv) removing the $P_i$ in the desorption solution.

In some embodiments, the immobilized PBP can be used for at least 5 adsorption/desorption cycles, alternatively at least 7 adsorption/desorption cycles, alternatively at least 10 adsorption/desorption cycles.

The methods described herein use a desorption solution with a pH of 11 or greater, preferably a pH of 11.4 or greater, more preferably having a pH of 12 or greater, for example, a pH of 12.5.

The methods described herein are able to facilitate quantification of concentrations of $P_i$ from about 0-50 μg/L in the original sample. In some embodiments, the concentration of the $P_i$ in the sample is from about 0-20 μg/L.

The liquid samples are any suitable liquid sample in which $P_i$ can be detected. For example, the liquid sample may be an environmental water sample, wastewater, or liquid laboratory sample. For example, suitable environmental water samples include, but are not limited to, river water, lake water, pond water, stream water or other water found in the environment.

Suitable wastewater samples include domestic wastewater or agricultural wastewater.

The present invention can further comprise a method of concentrating low levels of $P_i$ in a sample, the method comprising: (a) exposing a liquid sample to immobilized PBP for a sufficient amount of time to bind $P_i$ to the immobilized PBP within the sample; (b) desorbing the $P_i$ from the immobilized PBP by contacting the immobilized PBP with a desorption solution having a pH of 12 or greater, wherein the amount of the desorption solution is at least 2 times less than the starting volume of the sample. In some embodiments, the amount of the desorption solution is at least 10 times less than the starting volume of the sample. In some embodiments, the method further comprises (c) quantifying the $P_i$ within the desorption solution. This quantification may allow for the ability to determine the amount of $P_i$ in the original sample.

In some embodiments, the step (b) further comprises neutralizing the desorption solution containing the $P_i$ to a neutral pH with an acid. Suitably, a neutralized pH is from about 6-8, preferably about 6.8-7.5.

The methods described herein are able to desorb the $P_i$ from the immobilized PBP in a volume of desorption solution sufficient to concentrate the $P_i$ to a detectable level of more than 100 μg/L.

The present invention also provides kits for performing the methods described herein. For example, in one embodiment, the present disclosure provides a kit for quantifying ultra low levels of $P_i$ (e.g. levels below 100 μg/L, preferably less than 50 μg/L, or less than 20 μg/L) of $P_i$ in a liquid sample or concentrating $P_i$ from a liquid sample; the kit comprising (a) immobilized PBP, (b) a desorption solution having a pH of 11 or greater, preferably 11.4 or greater, most preferably pH of 12 or greater (e.g. pH of 12.5), (c) instructions for adsorbing and desorbing the $P_i$ from the immobilized PBP. In some embodiments, the immobilized PBP is PBP bound to a bead or membrane. In other embodiments, the immobilized PBP is PBP bound to a bacteria.

The present methods facilitate recovery of concentrated $P_i$ for more accurate measurements or as a phosphorus-rich product which can subsequently be used as agricultural fertilizer.

In one example, an engineered PBP (e.g., the high-affinity PstS protein, e.g., SEQ ID NO:5) system has been made comprising the PBP immobilized on a bead to ensure efficient separation from the liquid.

In one embodiment, the system for performing the methods of the present invention comprises purified PBP immobilized on inert surfaces or on the surface of bacteria cells. Suitable inert surface include glass, metal, silicon, plastic and agarose-based material shaped as beads or flat membranes which can be charged with a functional group that covalently binds to the proteins. These functional groups can include, e.g., Aldehyde, Glutaraldehyde, N-hydroxysuccinimide (NHS), Carbodiimide, Epoxides, Isothiocyanate, Azlactone, p-nitrophenyl. PBP can also be immobilized on bacteria by genetically modifying the bacteria with a plasmid that promotes expression of the PBP on the bacterial cell surface. Suitable PBP proteins for bacterial expression are known in the art.

Suitable methods of producing PBP are known in the art. For example, a recombinant bacteria cell modified to include a plasmid harboring the PBP gene may be used to express and purify the PBP. The bacterial cells are induced to over-express PBP proteins via either low $P_i$ conditions or PTG (isopropyl β-D-1-thiogalactopyranoside). The PBP proteins are extracted from the cells and purified.

The purified PBP are subsequently immobilized on an inert surface, e.g., Sepharose beads. The water sample is contacted with the immobilized proteins and allowed to bind with $P_i$ for 5 to 10 minutes or until the beads are saturated and can no longer remove additional $P_i$. Subsequently, the $P_i$ is released by controlling the desorption solution and desorption parameters. The desorption solution is preferably at a pH greater than 12 (e.g., pH of 12, 12.5, 13, etc or any pH range in between). It is this high pH solution that allows for the desorption and concentration of $P_i$. In one embodiment, the immobilized PBP may be operated in a flow-through column mode for $P_i$ removal and recovery in scaled-up applications.

In yet another embodiment, the system comprises E. coli bacteria modified to express the PBP protein on the cell surface using the ice nucleation protein as an anchor (See, e.g., SEQ ID NO:8, providing the gen sequence of the ice nucleation protein (anchor protein) and heterologous protein (PBP), which is known in the art (e.g. Chen and Georgiou (2002), among others). The bacteria is used in a similar fashion to the bead system, in that sample will be passed over the cells until saturation, followed by a regeneration period where adjustments to desorption parameters (e.g. pH of greater than 11, preferably pH of greater than 12 (e.g., 12.5)) will be used for controlled release of the concentrated $P_i$.

The PBP-based $P_i$ recovery systems, methods and compositions of the present invention offer several advantages over existing technology (e.g., ion exchangers) including, but not limited to, for example, (1) ability to achieve ultra-low $P_i$ concentrations (e.g. levels below 100 μg/L, preferably less than 50 μg/L, or less than 20 μg/L), even when starting at low levels (which surpass the ability of currently available ion exchangers), (2) operation in both wastewater matrices (e.g. where enhanced biological phosphorus removal is often employed) as well as in more dilute organic-poor environmental waters where ultra-low phosphorus regulations or guidelines may be implemented, and (3) enhanced selectivity for phospate (PBP is extraordinarily selective for $P_i$, with only one other ion —As(V)— known to attach at a much lower affinity). The ability to get more selective, reversible recovery of $P_i$ leads to separation of a more pure $P_i$-rich product. This in turn leads to higher value reuse applications. For example, in agriculture, the presence of heavy metals, pharmaceuticals, or other contaminants (which may be co-concentrated/released during ion exchange) in addition to the recovered phosphorus causes a problem for reuse.

The PBP systems and methods described herein provide improved separation and concentration to facilitate detection and reuse of low concentrations of $P_i$ in a range of water matrices, including environmental waters.

The PBP systems are believed to be able to capture phosphorus even more selectively compared to resins, which facilitates recovery of a more pure (thus, more valuable) phosphorus fertilizer product. Additionally, the proteins appear to be capable of removing $P_i$ even when it is present at initially low levels, providing improved performance over ion exchange resins in these conditions.

Immobilized PBP has advantages for removing $P_i$ from a variety of liquid matrices. Suitable liquid matrices in which the systems and methods can be used include, but are not limited to, for example, wastewaters including domestic, agricultural, and others, low-phosphorus environmental waters, drinking water, laboratory samples, and any other water sources in which $P_i$ is to be detected and/or removed. For example, in one embodiment, the methods described herein can be used in analytical labwork to improve $P_i$ quantification.

In addition to removing the $P_i$ from water matrices, the recovered product from use of the system and methods described herein is able to be used in phosphorus markets, for example, but not limited to, the production of agricultural fertilizer.

In an addition embodiment, the immobilized PBP proteins can be used in methods and systems for the capture and removal of As(V) from water, especially in water in which there are low levels of $P_i$. Additionally, the PBP proteins can be used in a second step of treatment of a water source in which $P_i$ had been first removed (i.e. by the method described herein) and exposed to a second step of contacting with the immobilized PBP proteins to bind any As(V) within the water source. The improved reusable adsorbents are needed that can efficiently remove As(V) from liquids (primarily drinking waters sources). Arsenic is a naturally occurring element, which can exist in four forms; arsenite (As(II)), arsenate (As(V)), arsenic (As(0)), and arsine (As (III)) (Nicomel et al., 2015). Among these four arsenic species, the most prevalent form in water is inorganic As(V) (Nicomel et al., 2015). As(V) is highly toxic to living organisms, and it is chemically and structurally similar to $P_i$, an indispensable nutrient for all life (Elias et al., 2012). Due to this similarity, As(V) can be incorporated into important biomolecules (DNA, ATP, etc.), causing irreparable damage to the cell (Elias et al., 2012). Accordingly, the World Health Organization (WHO) has established 0.01 mg/L as a guideline maximum concentration for arsenic in drinking water (Yamamura, 2001).

The premise behind this development is that improved reusable adsorbents are needed that can efficiently remove As(V) from liquids (primarily drinking waters sources). Arsenic is a naturally occurring element, which can exist in four forms; arsenite (As(III)), arsenate (As(V)), arsenic (As(0)), and arsine (As(III)) (Nicomel et al., 2015). Among these four arsenic species, the most prevalent form in water is inorganic As(V) (Nicomel et al., 2015). As(V) is highly toxic to living organisms, and it is chemically and structurally similar to $P_i$, an indispensable nutrient for all life (Elias et al., 2012). Due to this similarity, As(V) can be incorporated into important biomolecules (DNA, ATP, etc.), causing irreparable damage to the cell (Elias et al., 2012). Accordingly, the World Health Organization (WHO) has established 0.01 mg/L as a guideline maximum concentration for arsenic in drinking water (Yamamura, 2001). Toward this end, arsenic removal from drinking water to better protect human health is an important objective worldwide. In this invention, we are using immobilized PBPs to capture As(V), especially in water that may have low levels of $P_i$ such that the PBPs can preferentially bind As(V).

PBP can be used to adsorb As(V) by exploiting the physical and chemical similarity between As(V) and $P_i$. Additionally, the PBP will work as a reversible ligand such that we can release the concentrated As(V) back into solution in a controlled fashion for proper disposal and subsequent reuse of the PBP. For release of the As(V), we employ either 1) a high pH (pH>12.5) solution or 2) a solution containing excess $P_i$. The higher affinity of PBP towards $P_i$ as compared to As(V) would induce the PBP to replace any protein-bound As(V) with $P_i$, thereby desorbing As(V) from the protein. The PBP may be bound to an immobilized surface (e.g., bead or resin) or expressed by recombinant E. coli bacteria cells as described more herein. The immobilized proteins are introduced into the water matrix and allowed to bind with As(V) until they are saturated and can no longer remove additional As(V). Subsequently, the As(V) is released using a solution with excess $P_i$ or high pH (>12.5). This system would be operated in flow-through column mode for As(V) removal similar to as described for $P_i$ herein and release in scaled-up water treatment applications. Example 6 provides data showing the PBP can bind to, capture and release As(V) from water. Both $P_i$ and As(V) can be adsorbed at approximately 83% of the PBP-beads' theoretical adsorption capacity. After the adsorption phase, the PBP-beads were washed with a high pH (pH>12.5) buffer solution at 25° C. for 10 min. The results indicated that exposure to high pH conditions (>pH 12.5) released 90% and 80% of the adsorbed $P_i$ and As(V), respectively. Accordingly, PBP-beads can adsorb and desorb As(V) at levels similar to $P_i$. While PBP beads have a higher affinity for $P_i$ relative to As(V), in samples that have high As(V) and low $P_i$, the beads can bind to a majority of the As(V) which can then subsequently be released by subsequently adding a solution containing excess $P_i$ or high pH (greater than 12.5). As demonstrated in the Examples, PBP-beads can adsorb As(V) in neutral pH and desorb As(V) in high pH (pH 12.5). Additionally, As(V) can be desorbed from PBP-beads using a solution containing excess $P_i$.

Uses

Immobilized PBP proteins can be used in applications targeting selective capture and controlled release of $P_i$ in aqueous solution. In one example, the methods, kits and compositions of the present invention can be used for analytical $P_i$ measurements. The immobilized PBP protein can be used as a solid-phase extraction column in order to concentrate $P_i$ samples and, in some embodiments, undergo subsequent analysis (e.g., via the standard ascorbic acid method, ion chromatography, etc.) to quantify its presence. The concentration step enables quantification of $P_i$ when it is initially present in low concentrations precluding reliable quantification.

In another example, the present methods, compositions and kits can be used for water and wastewater treatment for removal and/or recovery of $P_i$. The immobilized PBP protein (e.g., PstS) can be used as a granular adsorbent media to selectively remove $P_i$ from complex aqueous matrices in order to meet water quality goals. Moreover, the removed $P_i$ can be released using high pH (e.g. pH 12) regenerant solution to regenerate adsorption capacity and facilitate recovery of concentrated $P_i$, which can then be reused, e.g., in agricultural fertilizer applications.

Figure 1B:
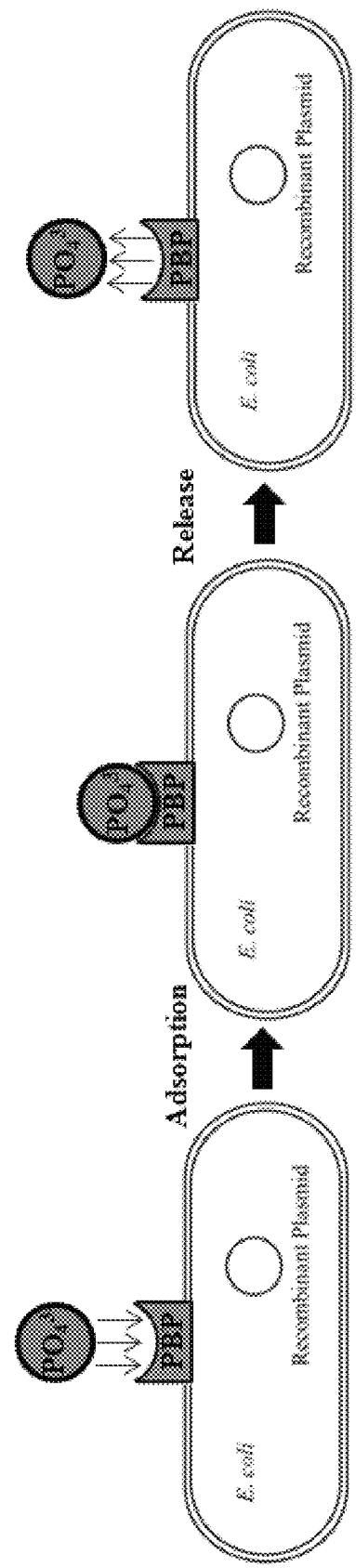
FIG. 1B is an illustration depicting the approach to using bacteria cells to over-express PBP on their surfaces. The PBP immobilized on the bacteria cells can then be used in adsorption applications.

A conceptual diagram showing the engineered systems (both recombinant bacteria expressing the protein and the PBP immobilized on a bead surface, as signified by the dotted lines) is presented in FIG. 1A. FIG. 1B shows an additional illustration showing $P_i$ recovery using engineered bacteria cells over-expressing PBP on the cell surface.

The present invention has been described in terms of one or more preferred embodiments, and it should be appreciated that many equivalents, alternatives, variations, and modifications, aside from those expressly stated, are possible and within the scope of the invention.

In another example, the present methods, compositions and kits can be used for water and wastewater treatment for removal and/or recovery of aresenate, especially in water sources having low $P_i$ or in water sources having previously been treated for removal of $P_i$. The immobilized PBP protein (e.g., PstS) can be used as a granular adsorbent media to selectively remove $P_i$ from complex aqueous matrices in order to meet water quality goals. Moreover, the removed As(V) can be released using high pH (e.g. pH 12) regenerant solution to regenerate adsorption capacity and facilitate proper disposal of the As(V). The PBP can then be reused for further methods.

The invention will be more fully understood upon consideration of the following non-limiting examples.

EXAMPLES

Example 1 Phosphate ($P_i$) Removal and Recovery Using Immobilized PBP

PstS is a ubiquitous, selective high affinity PBP. (Brune et al., 1998, 1994; Solscheid et al., 2015). PstS has been tested as a $P_i$ removal recovery system previously. (Choi et al., 2013; Kuroda et al., 2000; Yang et al., 2016) While the $P_i$ adsorption capabilities of PstS are well known, conditions that can provide controlled release of $P_i$ from PBP are not fully understood or characterized. Previous $P_i$ recovery studies did not show significant recovery potential using a wild type PstS. (Kuroda et al., 2000; Yang et al., 2016). Further, it was not known if the protein can be reused for multiple removal and recovery cycles. Reusability of the protein is crucial for making this system a viable alternative for $P_i$ removal and recovery.

The present Example demonstrates a comparison to wild type periplasmic PBP, extracellular PBP immobilized on an inert surface is more conducive to both removal and controlled recovery through specific regulation of environmental factors such as pH and temperature.

Materials and Methods

Expression and Purification of PBP

The PstS PBP used in this study was a single-cysteine mutant variant (A197C) of the mature *E. coli* PBP, developed by Solscheid et al. (2015) for use as a $P_i$ biosensor. A pET22b plasmid harboring the pstS gene (A197C) was procured as DH5alpha *E. coli* bacteria stab culture (plasmid #78198, Addgene, Cambridge, MA, USA). Following the depositor's protocol, the culture was initially streaked onto a Lysogeny broth (LB) agar plate containing 100 µg/mL ampicillin and incubated overnight at 37° C. A single colony was isolated and transferred into 5 mL LB solution augmented with 100 µg/mL ampicillin and grown overnight at 37° C. with vigorous shaking (200 rpm) to provide aeration. The overnight culture was centrifuged at 4000 rpm for 10 minutes and the plasmid from the resulting cell pellet was extracted using a QIAprep Spin Miniprep Kit (Qiagen©, Germantown, MD, USA). The extracted plasmid was introduced into BL21(DE3) *E. coli* competent cells, which were subsequently cultured for protein expression and purification using the procedure described by Solscheid et al. (2015).

A 5 mL overnight culture of the transformed BL21(DE3) cells was grown in LB medium containing 100 µg/mL ampicillin at 37° C. This culture was diluted by transferring 2 mL of the overnight culture into 1 L fresh LB growth media. The baffled glass flasks were incubated at 37° C. with vigorous shaking and the culture was allowed to grow to an OD 600 of approximately 0.8 before inducing protein expression using 500 µM IPTG. After 4-hour induction, cells were centrifuged for 15 min at 4000 G and 4° C.

To purify the cells, the pellets were re-suspended in 100 mL 10 mM Tris-HCl, 1 mM $MgCl_2$ pH 8.0 buffer solution and sonicated 4 times for 30 s at 200 W with a 5 s on/off pulse cycle. The lysate was decanted following centrifugation at 6000 G for 45 minutes. The lysate was passed through a 100 $mL_{BV}$ ($mL_{BV}$=settled bead volume) QSepharose column (GE Healthcare Bio-Sciences, Pittsburgh, PA, USA), previously equilibrated with 10 mM Tris-HCl, 1 mM $MgCl_2$ pH 8.0 buffer. The protein was eluted in a 100 mL gradient of 0-200 mM NaCl in 10 mM Tris-HCl, 1 mM $MgCl_2$ pH 8.0 buffer. The presence of the protein was verified in the eluted fractions using SDS-PAGE, followed by pooling of the fractions to yield 30 mL purified PBP. The concentration of the purified PBP was quantified as 221±0.6 µM (average±standard deviation) using a Quick Start™ Bradford Protein Assay (Bio-Rad Laboratories Inc., Hercules, CA, USA).

Immobilization of PBP

The purified PstS PBP was immobilized on NHS-activated Sepharose 4 Fast Flow beads in accordance with the manufacturer's instructions (GE Healthcare Bio-Sciences). A Spectra/Por 2 Dialysis Membrane (MWCO 12-14 kDa, Spectrum Laboratories, Inc., Rancho Dominguez, CA, USA) was used to dialyze the PBP. Dialysis was conducted for 16 hours at 4° C. and included 6 exchanges of 0.2 M $NaHCO_3$, 0.5 M NaCl pH 8.3 buffer. The Bradford Protein Assay was used to quantify the concentration of the dialyzed PBP as 202±2 µM.

Fresh NHS beads (GE Healthcare Bio-Sciences, stored in 100% isopropanol) were transferred into a 100 mL Econo-Column® (Bio-Rad Laboratories Inc.) and washed with 10 bed volumes ($10_{BV}$) 4° C. 1 mM HCl solution. For the coupling reaction, 20 mL of dialyzed PBP solution was loaded into the Econo-Column® containing 20 mL of washed NHS beads. The Econo-Columns was mixed at 30 rpm on an end over end rotator for 16 hours at 4° C. to promote coupling. The flow through was collected and analyzed for PBP concentration using the Bradford assay. Of the initial PBP loaded onto the column (202±2 µM), 98±0.6% was immobilized onto the NHS beads, providing a coupling density of 197±0.2 nmoles $PBP/mL_{BV}$ NHS beads. Knowing that 1 mole of PBP can adsorb 1 mole of $P_i$ (Brune et al., 1998, 1994; Solscheid et al., 2015), the theoretical $P_i$ adsorption capacity of the PBP beads was 197±0.2 nmoles/$mL_{BV}$. In accordance with manufacturer instructions, the PBP beads were washed with $1_{BV}$ (settled bead volume, where BV=bed volume) of 0.1 M Tris-HCl buffer pH 8.5 followed by 1V 0.1 M acetate, 0.5 M NaCl buffer pH 4.5. This cycle was repeated 3 times followed by five washes with 1V 10 mM Tris-HCl, 1 mM $MgCl_2$ pH 7.0 buffer.

To remove any $P_i$ that already adsorbed on the PBP during the expression, purification and immobilization process, the PBP beads were mopped using 0.1 unit/mL purine nucleoside phosphorylase (PNPase) and 300 µM 7-methylguanosine (7-MEG) (Brune et al., 1998, 1994). To facilitate mixing, 20 mL of 10 mM Tris-HCl, 1 mM $MgCl_2$ pH 7.0 buffer was added to 20 $mL_{BV}$ PBP beads. Next, 0.1 unit/mL PNPase enzyme and 300 µM 7-MEG was added to the 40 mL PBP bead solution (50% suspension). The mopping reaction was carried out overnight at 4° C. at 30 rpm using a rotary shaker. After 16 hours, the PBP beads were washed with 5×1V 10 mM Tris-HCl, 1 mM $MgCl_2$ pH 7.0 buffer to remove the $P_i$-mop. This concluded the PBP immobilization procedure and these beads, which from hereon will be referred to as PBP beads, were either used immediately or stored at 4° C. for up to 48 hours prior to use.

A control set of beads was prepared using 20 $mL_{BV}$ of fresh NHS beads following the same procedure used for the PBP bead, except without the addition of PBP.

Recovery of $P_i$ from Immobilized PBP as a Function of Temperature and pH

Triplicate $P_i$ recovery experiments were conducted in batch tests in 2 mL centrifuge tubes containing 0.25 $mL_{BV}$ PBP beads. In all tests, excess $P_i$ was initially added, 60 µM versus the maximum theoretical capacity of the PBP beads of 197±0.2 nmoles/$mL_{BV}$ (or 49 nmoles/0.25 $mL_{BV}$), to ensure maximum adsorption. Tubes were gently mixed, and then the beads were allowed to settle for 10 min. A 1 mL aliquot was analyzed for $P_i$ using the standard ascorbic acid method (APHA, 2012). The beads were washed 3 times using 1 mL 1× buffer pH 7 to remove unbound $P_i$. Each tube was then loaded with 1 mL of 1× buffer (10 mM Tris-HCl, 1 mM $MgCl_2$) solution. In separate experiments, the influence of temperature was evaluated by adjusting the buffer temperature to 25° C., 35° C., or 45° C. (pH 7). Additional tests were performed to evaluate the influence of pH by adjusting 25° C. buffer to final values of 4.7, 6.5, 7.1, 8.5, 9.2, 11.4, 12.5 using 1 M HCl or NaOH. The pH in the tubes was measured using a micro pH probe (Orion™ 9810BN, Thermo Scientific™, Waltham, MA, USA). The beads were gently mixed, allowed to settle for 10 min before 1 mL aliquot was collected and analyzed for $P_i$. For each condition tested, controls were tested in parallel using control beads in place of PBP beads.

Kinetics of $P_i$ Recovery from Immobilized PBP

The extent of $P_i$ release from PBP beads was assessed as a function of time for 4 different pH conditions. Triplicate experiments were conducted for both PBP beads and control beads. An initial $P_i$ adsorption cycle was performed by adding 1 mL of 60 µM $P_i$ solution in 1× buffer at pH 7 and 25° C. to the beads. The supernatant was collected and analyzed for $P_i$ concentration. The beads were then washed 3 times with 1 mL 1× buffer pH7 to remove the $P_i$ solution. Next, the beads were washed with 1.5 mL of 1× buffer, yielding final pH values in the tubes of 7.06, 10.82, 11.88 and 12.5. Aliquots of 0.2 mL were collected for $P_i$ analysis after 5, 10, 20, 30, 40 and 50 minutes of reaction.

Reusability of Immobilized PBP

Figure 2:
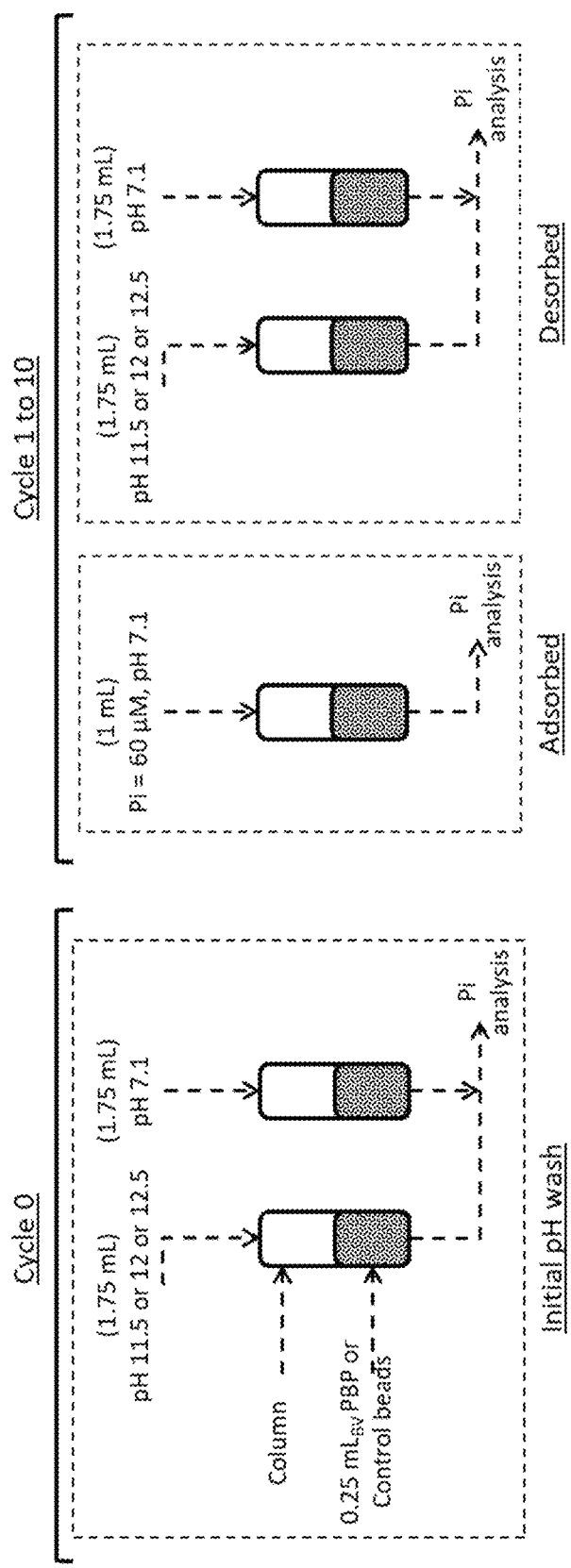
FIG. 2: Illustration of the PBP bead reusability experiment. The experiment was conducted in triplicate Poly-Prep® columns with 0.25 $mL_{BV}$ of PBP and control beads without PBP. Cycle 0 includes 2 steps: 1) initial $P_i$ desorption wash and 2) neutral pH wash. Cycles 1 to 10 include 3 steps that were repeated 10 times: 1) $P_i$ adsorption, 2) high pH $P_i$ desorption and 3) neutral pH wash.

The ability of the PBP beads to adsorb and desorb $P_i$ over 10 cycles of high and neutral pH (promoting desorption and adsorption, respectively) was investigated. Tests were conducted in 10 mL disposable Poly-Prep® columns with 0.25 $mL_{BV}$ of beads. Although operated in batch mode, the columns were more convenient than centrifuge tubes for processing multiple cycles. Based on results of previous pH tests, 3 different high pH conditions, 11.5, 12 and 12.5, were tested in independent triplicate experiments using PBP beads or control beads. FIG. 2 provides the illustration of the experimental procedure used. The first step in these experiments was to release any $P_i$ previously adsorbed on the PBP beads by washing them for 10 min with 1.75 mL of 1× buffer at 25° C. at pH 11.5, 12 or 12.5. Immediately after this, 1.75 mL 1× buffer at pH 7.1 and 25° C. was added to adjust the beads to near neutral pH for the subsequent $P_i$ adsorption cycle.

Following the initial $P_i$ release step, 10 cycles of $P_i$ adsorption/desorption were performed. The first step in each cycle consisted of 10 min $P_i$ adsorption using 1 mL 1× buffer at pH 7 and 25° C. containing 60 µM of $P_i$ In the second step, $P_i$ was desorbed using 1.75 mL of 1× buffer at 25° C. and pH 11.5, 12 or 12.5 for 10 minutes. In the third step, 1.75 mL 1× buffer at pH 7.1 and 25° C. was added for 10 minutes to wash away any remaining high pH buffer.

Data Analysis

All PBP bead $P_i$ concentration data was normalized to the corresponding control bead tested. The normalized data was also compared to the theoretical maximum $P_i$ adsorption capacity of the PBP beads, to obtain percent $P_i$ adsorbed and desorbed data. Statistical differences in $P_i$ concentrations between different conditions were assessed using one-way ANOVA conducted on Excel 2010 (Version 14.3.2 e Microsoft, USA) with an added statistical software package XLStat Pro 2014 (Addinsoft, USA).

Results and Discussion $P_i$ Removal from Immobilized PBP 0.25 mL of PBP beads should adsorb 49 nmoles of $P_i$. However, the PBP beads only adsorbed 11.84 nmoles $P_i$ (n=39) or 248% of the theoretical capacity. One possible reason for the low $P_i$ adsorption could be that the PBP active sites are already bound to $P_i$ ions. Previous studies have successfully applied PNPase (0.1 unit/mL) and 7-MEG (300 µM) to mop PBP (Brune et al., 1998, 1994). However, there are no reported studies which have applied PNPase and 7-MEG to mop immobilized PBP. Subsequent recovery experiments with PBP beads confirmed that the observed low adsorption capacity was due to insufficient removal of contaminant $P_i$ ions.

Recovery of $P_i$ as a Function of Temperature and pH

The temperature range tested in this study did not show any influence on $P_i$ recovery (p value<0.05, n=3). The $P_i$ released from the PBP beads after 10 minute exposure to 25° C., 35° C. and 45° C. was 1.6±5.1 nmoles, 3.9±1.3 nmoles and 4.5±3.5 nmoles, respectively. On the other hand, pH was observed to have a strong influence on $P_i$ desorption. Exposure to a pH of 4.7, 6.5, 7.1, 8.5, 9.2, 11.4 and 12.5 released 7.92 nmoles $P_i$, 1.9±2.4 nmoles $P_i$, 1.6±5.1 nmoles $P_i$, 6.7±4.9 nmoles $P_i$, 14.7±4.3 nmoles $P_i$, 30.2±3.9 nmoles $P_i$ and 42.2±5.5 nmoles $P_i$, respectively.

It is important to note that $P_i$ released at pH 11.4 (30.2±3.9 nmoles) and 12.5 (42.2±5.5 nmoles) was significantly higher (p value<0.05, n=3) than the amount that was adsorbed by the PBP beads (11.8±4 nmoles). This confirms that $P_i$ ions were previously bound to the PBP, which resulted in decreased $P_i$ adsorption capacity.

Figure 3:
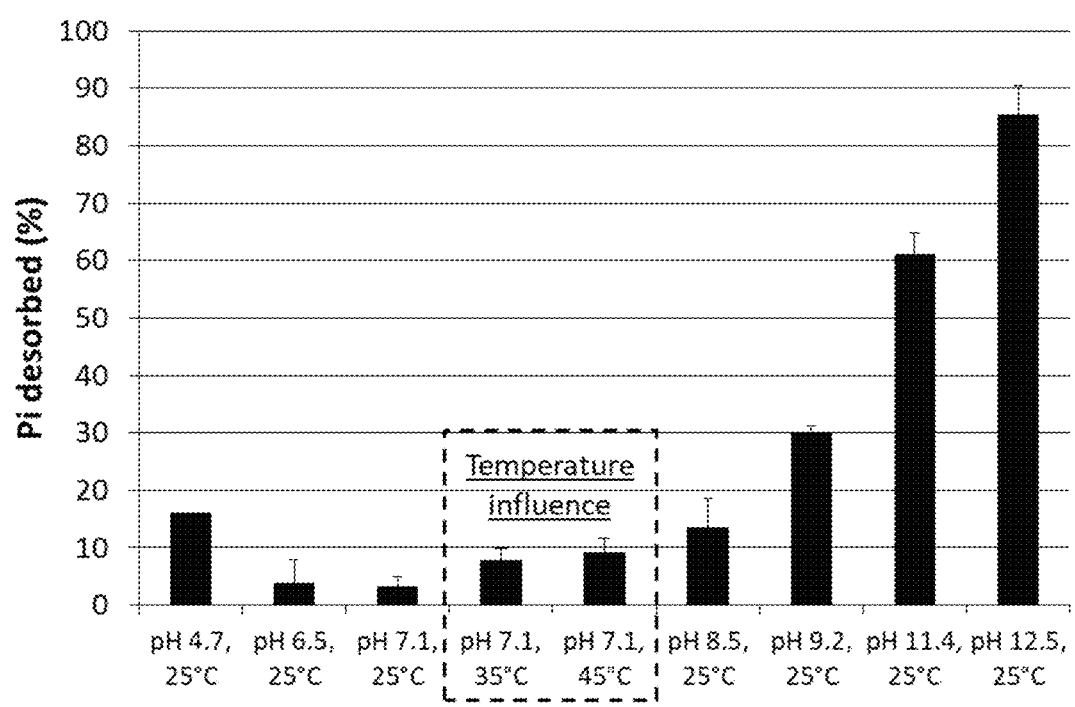
FIG. 3: $P_i$ recovery from 0.25 $mL_{BV}$ PBP beads at varying pH and temperature. The Y axis represents percent $P_i$ desorbed out of the theoretical adsorption capacity (49 nmoles/0.25 m $L_{BV}$). The X axis describes the 1× buffer pH and temperature condition during the test. The error bars represent the standard deviation from triplicate analysis.

For the purpose of $P_i$ recovery, pH>12 was observed to be the ideal condition for inducing $P_i$ release. Exposing the PBP beads to pH 11.4 and 12.5 released 62% and 86%, respectively, of the theoretical $P_i$ adsorption capacity (49 nmoles/ 0.25 $mL_{BV}$) (FIG. 3).

Kinetics of $P_i$ Recovery from Immobilized PBP

Figure 4:
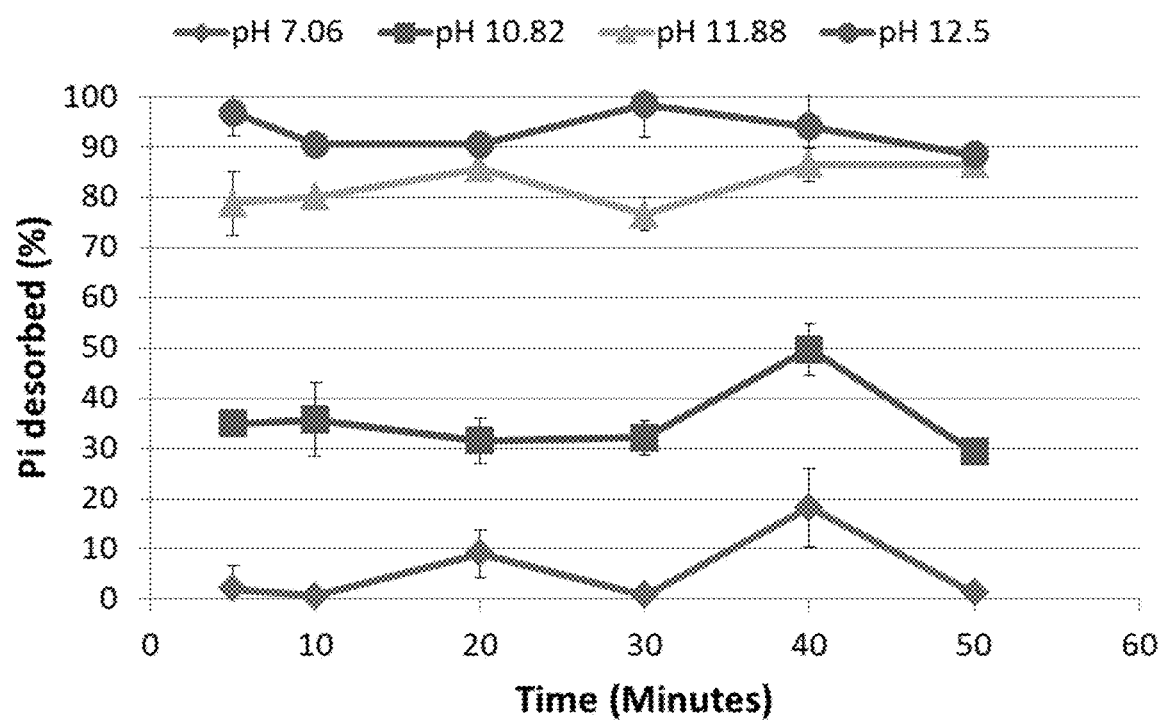
FIG. 4: Kinetics of $P_i$ recovery from 0.25 $mL_{BV}$ PBP beads at varying pH. The Y axis represents percent $P_i$ desorbed out of the theoretical adsorption capacity (49 nmoles/0.25 $mL_{BV}$). The X axis represents exposure time in minutes. All tests were conducted in 1× buffer at 25° C. and the pH conditions are described in the legend. The error bars represent the standard deviation from triplicate analysis.

The exposure time did not show any influence on $P_i$ desorption, in all pH conditions tested (FIG. 4). The $P_i$ released after 5 and 50 minutes exposure were statistically the same (p value<0.05, n=3).

However, pH did have a significant influence on $P_i$ desorption. The average percent $P_i$ (or nmoles $P_i$) desorbed within 5 minutes of exposure to pH 7.06, 10.82, 11.88 and 12.5 was 2±9.6% (1±4.8 nmoles), 35±4.4% (17±2.1 nmoles), 79±13% (39±6 nmoles), and 97±9.4% (48±4.6 nmoles), respectively.

This indicates that high pH condition, not exposure time, is the important factor for inducing $P_i$ release. It is possible that the $P_i$ release occurs instantaneously after exposure, which can be an advantageous feature for a $P_i$ removal and recovery system and should be further investigated.

Reusability of Immobilized PBP

For the immobilized PBP to be a viable $P_i$ removal and recovery system, it is important that PBP is reusable after being exposed repeatedly to the conditions that induce $P_i$ release.

Figure 5:
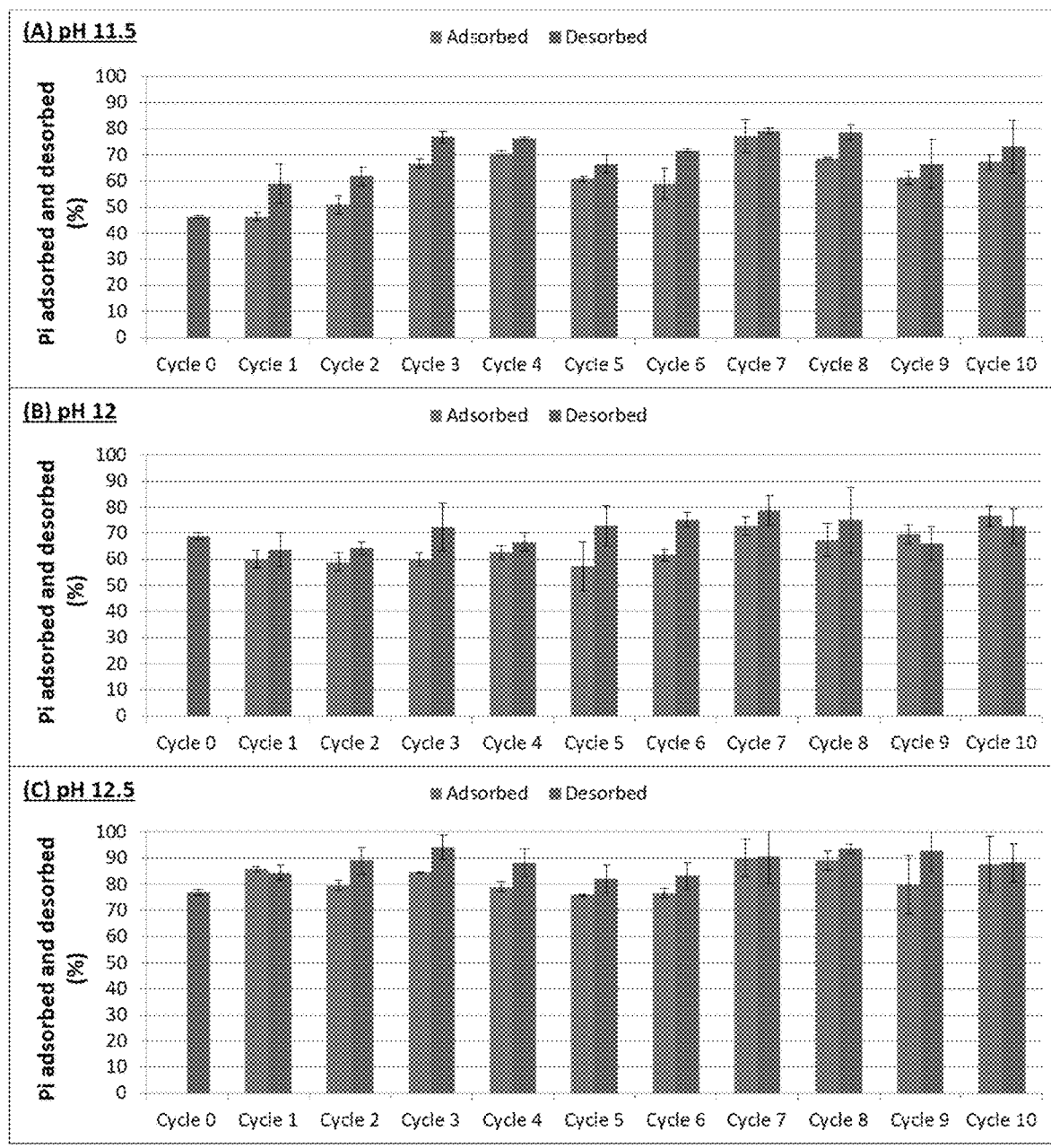
FIG. 5: Summary of PBP bead reusability experiment showing 10 repetitive cycles of $P_i$ adsorption at pH 7.1 and $P_i$ desorption at (A) pH 11.5, (B) pH 12 and (C) pH 12.5. The Y axis represents percent $P_i$ adsorbed and desorbed out of the theoretical adsorption capacity (49 nmoles/0.25 $mL_{BV}$). In the X axis, Cycle 0 represents the initial $P_i$ desorption wash and Cycles 1-10 represent the subsequent 10 $P_i$ adsorption and desorption cycles. All tests were conducted in 1× buffer at 25° C. The error bars represent the standard deviation from triplicate analysis.

From the initial $P_i$ desorption wash (Cycle 0), the average percent $P_i$ (or nmoles $P_i$) desorbed at pH 11.5, 12 and 12.5 was 46±0.6% (or 23±0.3 nmoles), 69±1.2% (or 34±0.6 nmoles) and 77±1.2% (or 38±0.6 nmoles), respectively (FIG. 5).

FIG. 5 shows the PBP bead's $P_i$ adsorption and desorption capacity after 10 repetitive cycles of exposure to pH 11.5, 12 and 12.5. No decreasing trend in PBP bead's $P_i$ adsorption or desorption capacity can be observed.

Between Cycle 1 and Cycle 10, the average percent $P_i$(or nmoles $P_i$) adsorbed by PBP beads exposed to pH 11.5, 12 and 12.5 was 63±8.8% (31±4.3 nmoles), 65±6.2% (32±3 nmoles) and 83±5% (41±2.5 nmoles), respectively (FIG. 5).

The average percent $P_i$(or nmoles $P_i$) desorbed between Cycle 1 and Cycle 10 by pH 11.5, 12 and 12.5 PBP beads were 71±6.8% (35±3.3 nmoles), 715% (35±2.5 nmoles) and 89±4.1% (44±2 nmoles), respectively.

The average $P_i$ adsorbed and desorbed over 10 cycles were statistically similar (p value<0.05, n=30) for all pH conditions, i.e., all $P_i$ adsorbed by PBP beads can be recovered.

The PBP beads successfully demonstrated that they can remove and recover $P_i$ for at least 10 cycles, with the highest average $P_i$ adsorption/desorption condition being pH 12.5, followed by pH 12 and pH 11.5 at room temperature.

Example 2: Concentration of $P_i$ from Environmental Water Samples

The PBP-beads were tested for $P_i$ adsorption from environmental water samples, with subsequent $P_i$ release in a concentrated solution.

Figure 6:
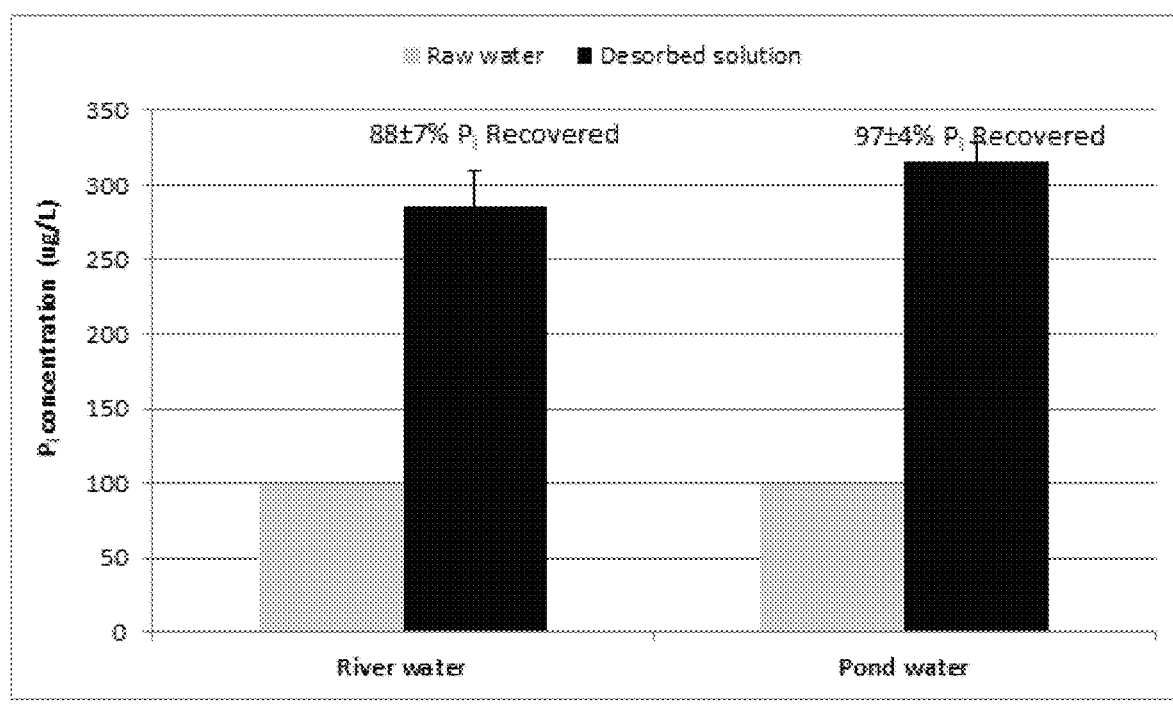
FIG. 6: $P_i$ concentration in the raw environmental waters and desorbed $P_i$ isolution. The $P_i$ concentration in desorbed $P_i$ solution were 2.9 and 3.2 times higher than in the raw river and pond samples, respectively. The total $P_i$ adsorbed and recovered was 88% and 97% of the total $P_i$ present in the raw river and pond water, respectively.

Two different environmental water samples (river and pond) with 100 μg/L $P_i$ were tested. The results show that the PBP-beads can successfully adsorb and desorb $P_i$ from environmental water samples, with $P_i$ concentrations as low as 100 μg/L The average P recovered from PBP-beads was 88 and 97% of the total $P_i$ present in the river and pond water, respectively (FIG. 6).

The P concentration in the desorbed solution was 2.9 to 3.2 times higher than in the raw water samples.

The results demonstrate that PBP-beads can adsorb and release $P_i$ in a concentrated solution from environmental water samples.

PBP Source

The wildtype PstS gene is sourced from *E. coli* K12 bacteria. The wildtype PstS gene can be modified to remove its signal peptide sequence or to include an affinity tag sequence. The affinity tag can be a histidine chain (His-tag), glutathione S-transferase (GST-tag) or chitin binding domain (CBD-tag). The tag sequence can be inserted at either the N or C terminus of the PstS gene sequence.

The PstS gene is cloned in an appropriate expression vector (e.g., the pET21b+plasmid) and transformed into an appropriate expression host cell (e.g., BL21 DE3 *E. coli* cells).

Example 3: $P_i$ Adsorption in the Presence of Common Environmental Water and Wastewater Anions In this example, experimental results indicated that the PBP-beads can effectively adsorb $P_i$ in the presence of competing anions commonly found in environmental waters and wastewaters (Venkiteshwaran et al., 2020, incorporated by reference in its entirety).

PBP proteins were immobilized onto NHS activated sepharose beads in accordance with the manufacturer's protocols (GE life sciences, Marlborough, MA, USA). More than 98% of the PBP protein added was successfully immobilized onto the NHS activated beads.

$P_i$ adsorption by PBP beads was analyzed at 3 different concentrations of anion mixtures containing $Br^-$, $NO_2^-$, $NO_3^-$, $SO_4^{2-}$, and $HCO_3^-$ (dosed using the respective salt: $NaBr$, $NaNO_2$, $NaNO_3$, $Na_2SO_4$, and $NaHC_3$). These mixtures represent common water/wastewater anions and their variations in concentration in most environmental water and treated wastewater effluent. No $Cl^-$ was added as the reaction buffer (10 mM Tris-HCl, 1 mM $MgC_2$ at pH 7.1) itself contained approximately 530 mg/L $Cl^-$ due to the presence of $MgCl_2$ and addition 1 M HCl to adjust the reaction buffer pH. The control set was analyzed using the reaction buffer with no added anions. The high anion concentration reaction buffer contained 6 mg/L $Br^-$, 6 mg/L $NO_2^-$, 4 mg/L $NO_3^-$, 102±3 mg/L $SO_4^{2-}$, and 120 mg/L $HCO_3^-$. The low anion concentration reaction buffer was prepared by diluting the high anion concentration reaction buffer by half using reaction buffer with no added anions. The pH of the low and high anion reaction buffer was readjusted to 7.1.

The experiments were conducted in triplicate batch tests in 10 mL Econo-Columns containing 0.1 $mL_{BV}$ PBP beads at constant temperature and pH (22° C., pH 7.1). At each anion concentration, triplicate sets of PBP beads were exposed to 10 mL reaction buffer containing 9 different $P_i$ concentrations (0.15, 0.25, 0.5, 0.75, 1, 1.25, 1.5, 1.75, or 2 μM $P_i$). After adding the reaction buffer, the columns were closed and mixed at 30 rpm on a Roto-Torque Variable Speed end-over-end rotator for 60 min. The reaction buffer was then collected and analyzed for $P_i$. A parallel set of control beads tests was performed. The theoretical capacity of the PBP beads in these experiments was 88 nmol-$P_i$/$mL_{BV}$.

Figure 7:
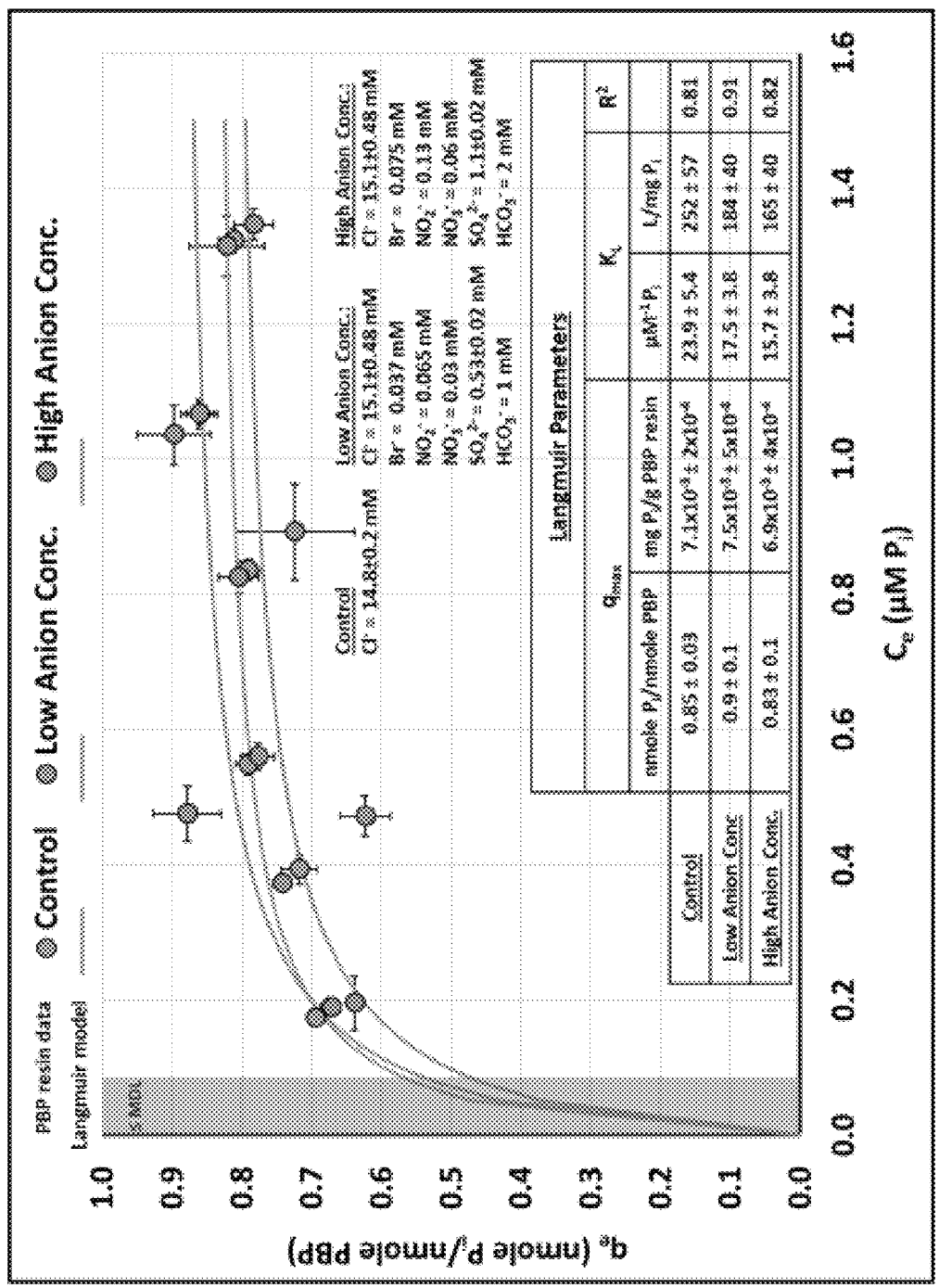
FIG. 7: Influence of low and high anion concentration on PBP beads $P_i$ adsorption at constant temperature and pH (22° C., pH 7.1), along with the estimated Langmuir isotherm parameters. The vertical and horizontal error bars represent the standard deviation of triplicate analyses. Only $q_e$ (nmoles of $P_i$ adsorbed per nmoles of PBP) and $C_e$ (concentration of $P_i$ in water at equilibrium) values corresponding to $C_e$ values≥the minimum detection limit (MDL) of 0.09 µM are shown in the plot and used to fit the Langmuir model. The maximum $P_i$ adsorption capacity ($q_{max}$) and the $P_i$ affinity (Langmuir constant ($K_L$)) were similar at all anion concentrations tested (p>0.05).

Results: The influence of low and high anion concentrations on PBP beads $P_i$ adsorption at constant temperature and pH (22° C., pH 7.1) along with the estimated Langmuir isotherm parameters is shown in FIG. 7. The $Cl^-$ concentration in the reaction buffer was initially high (≈530 mg/L) due to the addition of 1 N HCl to bring the buffer pH to 7.1. Therefore, the presence of high $Cl^-$ ions did not affect the $P_i$-PBP beads adsorption process based on the range of experiments conducted using the reaction buffer in this study. Compared to the control condition (no added anions), the presence of other common water/wastewater anions ($Br^-$, $NO_2^-$, $NO_3^-$, $SO_4^{2-}$, and $HCO_3^-$) at low and high anionic concentrations did not significantly influence the PBP beads' adsorption capacity or $P_i$ affinity. These results confirm that the PBP beads can maintain its $P_i$ adsorption capacity, affinity, and selectivity in the presence of high anion concentrations, thereby supporting its potential as a $P_i$ adsorbent in real water or wastewater applications.

Example 4: Concentration of Ultra-Low $P_i$ from Water Samples

The PBP-beads were tested for $P_i$ adsorption from synthetic laboratory water samples containing ultra-low $P_i$ concentrations, with subsequent $P_i$ release in a concentrated solution. This approach concentrates the $P_i$ such that it can either be recovered as a value-added product (e.g., nutrient-rich fertilizer product) or for further quantification using known laboratory techniques.

Figure 8:
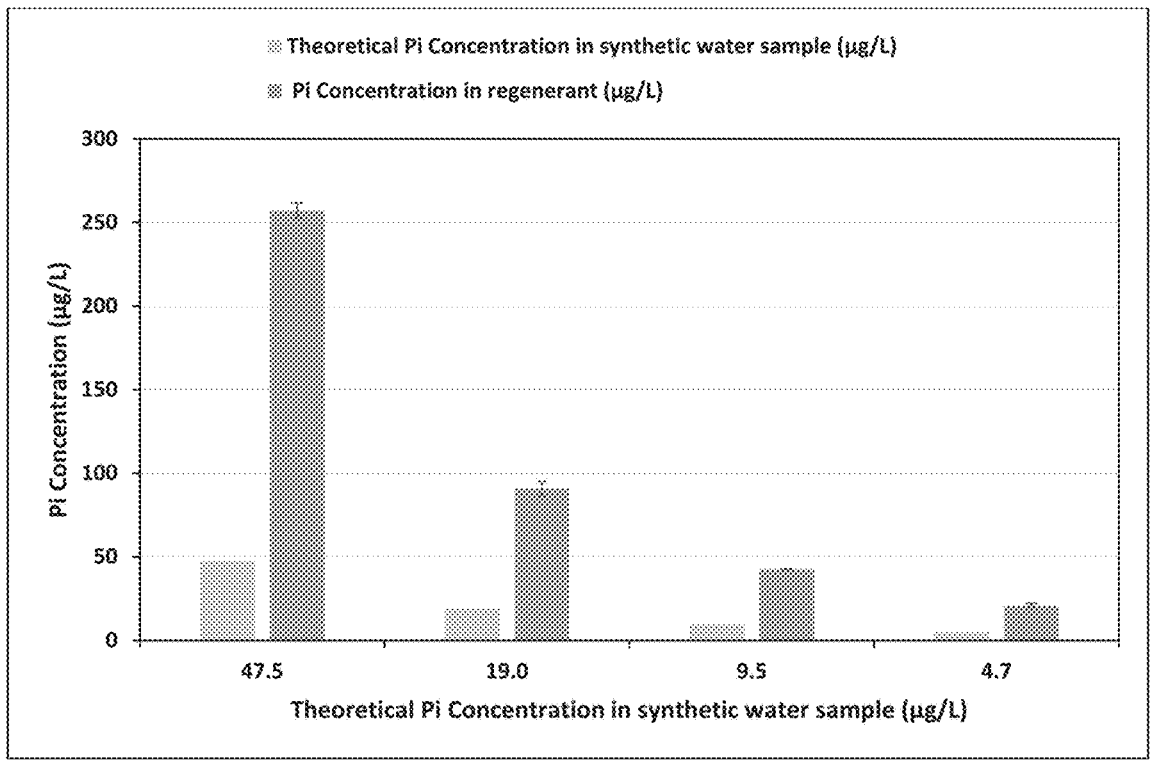
FIG. 8: Initial theoretical $P_i$ concentration in the synthetic water samples containing ultra-low $P_i$ concentrations ranging from 4.7 to 47.5 µg/L and the measured $P_i$ concentration in the desorbed concentrated regenerant solution. The $P_i$ concentrations in the desorption solution (pH 12.7) were 4.4 to 5.4 times higher than in the synthetic water samples. The total $P_i$ adsorbed and recovered ranged from 89% to 100% of the total $P_i$ originally present in the water samples.

Four different synthetic laboratory water samples with low $P_i$ concentrations—47.5 µg/L, 19 µg/L, 9.5 µg/L and 4.7 µg/L—were tested. The results showed that the PBP-beads can successfully adsorb and desorb $P_i$ from water samples with ultra-low $P_i$ concentration ranging from 4.7-47.5 µg/L (FIG. 8). The average $P_i$ recovered from the PBP-beads ranged from 89% to 100% of the total $P_i$ originally present in the water samples tested. The $P_i$ concentration in the desorbed solution was 4.4 to 5.4 times higher than in the synthetic water samples.

$P_i$ was quantified in the synthetic water samples and in the concentrated regenerant using a conventional colorimetric technique (Standard Method 4500-P E, the Ascorbic Acid method, APHA, 2012, (American Public Health Association (APHA); American Waterworks Association (AWWA); Water Environment Federation (WEF). 2012. *Standard Methods for the Examination of Water and Wastewater. Standard Methods*. New York, NY, USA.: McGraw-Hill Companies, Inc. https://doi.org/ISBN 9780875532356.).

Figure 9:
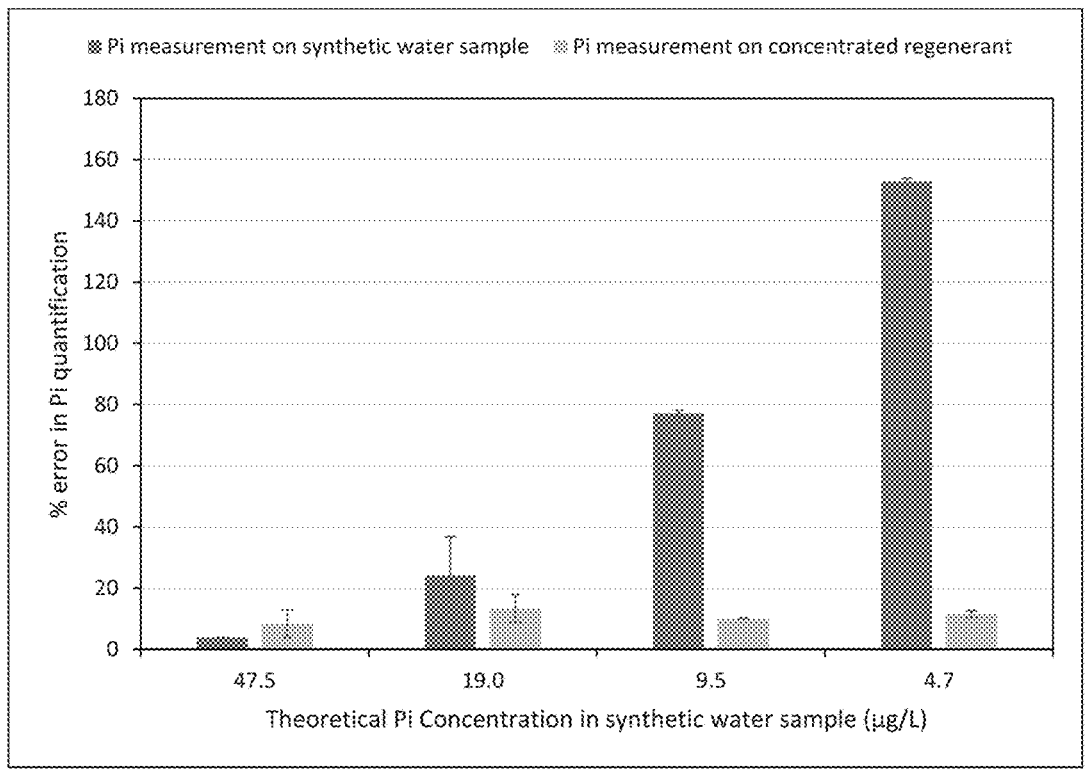
FIG. 9: Percent error in $P_i$ quantification in the synthetic water samples containing ultra-low $P_i$ concentrations ranging from 4.7 to 47.5 µg/L and in the desorbed concentrated regenerant solutions. The percent error in $P_i$ quantification in the concentrated regenerant, recovered from synthetic water samples containing ultra-low $P_i$ concentrations was much lower compared to the initial samples.

For each sample, the difference between the known mass $P_i$ (based on initial spiked amounts) per volume solution was calculated. The results are presented in FIG. 9 as "percent error in $P_i$ quantification". As shown, higher percent errors in $P_i$ quantification were observed in the synthetic water samples containing ultra-low $P_i$ concentration: 24% error for the 19 µg/L sample, 77% error for the 9.5 µg/L sample, and 153% error for the 4.7 µg/L sample. Alternately, much lower $P_i$ quantification errors were observed in the concentrated regenerant recovered from synthetic water samples containing ultra-low $P_i$ concentrations: 13% error for the concentrated 19 µg/L sample, 10% for the concentrated 9.5 µg/L sample, and 11% error for the concentrated 4.7 µg/L sample.

Example 5: Suitable Methods for Use in the Present Invention

PBP Production

The transformed *E. coli* expression cells are grown to an optical density (OD) of 0.8 in Luria Broth at 37° C. and induced with 1 mM Isopropyl β-D-1-thiogalactopyranoside (IPTG). The cells are harvested by centrifugation at 4000×g for 15 min and 4° C. The PstS protein is then extracted from the cells by lysis by methods known in the art. For example, suitable lysis procedures include enzymatic digestion (lysozyme treatment), freeze thaw, ultrasonic treatment, and the like.

PBP Purification

The untagged PstS can be purified using a Q-Sepharose bead column following established protocols (GE Healthcare Bio-Sciences, Pittsburgh, PA, USA). The PstS tagged with a His-tag, GST-tag, or CBD-tag is purified using a sepharose bead incorporated with $Ni^+$-NTA, glutathione, or chitin, respectively, following established protocols (GE Healthcare Bio-Sciences, Pittsburgh, PA, USA). Use of a tagged Psts protein has the advantage of providing a higher purity product after the purification step.

PBP Immobilization

Several products are commercially available for immobilizing proteins onto inert beads. The untagged and His-tagged PstS can be immobilized onto NHS-activated sepharose beads following established protocols (GE Healthcare Bio-Sciences, Pittsburgh, PA, USA). PstS tagged with a GST-tag or CBD-tag can be purified using glutathione or chitin sepharose beads, respectively. The advantage of GST-tagged or CBD-tagged PstS is that protein purification and immobilization can be performed in a single step.

$P_i$ Desorption $P_i$ adsorbed on the immobilized PstS can be desorbed by exposing the PstS to a high pH condition. Desorption solutions used herein should have a pH greater than 11, preferably a pH of greater than 11.4, for example, but not limited to, e.g., pH 11.4, pH 12, pH 12.5 or greater, among others. For maximum desorption, the pH should be adjusted to >12. Following the high pH desorption step, the PstS is washed with a neutral pH solution and maintained at pH 7 in preparation for subsequent adsorption/desorption cycles.

After initial desorption to remove $P_i$, the immobilized PstS is ready for $P_i$ adsorption. Filtered water samples can be passed through these beads for $P_i$ adsorption. Subsequently, $P_i$ can be desorbed in a concentrated form by passing a high pH solution (pH 12 to 13) through the beads. The pH of the desorbed $P_i$ solution can be neutralized using an acid (e.g., HCl) and used for subsequent processing.

The immobilized PstS beads have demonstrated $P_i$ adsorption at levels greater than 85% the maximum theoretical $P_i$ capacity (based on 1:1 $P_i$:PstS binding), with 100% $P_i$ desorption at pH 12 or higher, for at least 10 sequential cycles.

A sequence listing in text format is concurrently submitted and is incorporated into this Specification in its Entirety.

Example 6: Immobilized PBP can Effectively Discriminate Against As(V) During $P_i$ Adsorption and Recovery In this example, experimental results indicated that the PBP-beads can remove As(V) if the water source has low or undetectable levels of phosphate.

The experimental results in this example also shows that the PBP-beads preferentially adsorb $P_i$ over As(V) (anticipated to be the main competitor) if both As(V) and $P_i$ are present in detectable levels.

Increasingly lower phosphorus guidelines are being implemented to reduce economic and ecological losses associated with eutrophication of environmental waters. Meanwhile, phosphorus is also a necessary nutrient for agriculture. This provides a strong impetus to stimulate a circular phosphorus economy by recovering waste P for reuse as agricultural fertilizers, i.e., via phosphorus recovery from wastewater (Mayer et al., 2016; Venkiteshwaran et al., 2018).

Adsorption technologies such as ion exchange resins have attracted considerable interest for inorganic $P_i$ removal and recovery from wastewater (Kumar et al., 2019). Ion exchange has the ability to remove $P_i$ to low levels (30 to 300 µg $P_i$/L), and release $P_i$ under controlled conditions (Mayer et al., 2013; SenGupta and Cumbal, 2007). Commercially available $P_i$ ion exchange resins are unaffected by the presence of typical ions found in wastewaters such as $Cl^-$, $F^-$, $SO_4^{2-}$ and $CO_3^{2-}$ (Acelas et al., 2015; Blaney et al., 2007; You et al., 2016). However, one concern that has not been adequately addressed is that some wastewaters targeted for P recovery may also contain elevated concentrations of the toxic metalloid arsenic, with reported concentrations in urine, manure, and sewage ranging from ~100 µg/L up to ~15 mg/L (Calderon et al., 1999; Cortinas et al., 2006; Phyllis2 Database, 2020; Ronteltap et al., 2007). As(V), or arsenate ($AsO_4^{3-}$), is the most common form of arsenic found in wastewater and closely resembles the structure of $P_i$. Due to its similarity to $P_i$ with respect to configuration, chemical properties, and ionic radii (2.48 Å for As(V) vs 2.38 Å for $P_i$), As(V) can readily substitute for $P_i$ during struvite precipitation and at adsorbent binding sites (Cullen and Reimer, 1989; Marcus, 1997). For example, As(V) is removed along with $P_i$ in struvite minerals precipitated from urine (Ronteltap et al., 2007) and sewage sludge anaerobic digestate (Uysal et al., 2010). Similarly, $P_i$ ion exchange resins fail to discriminate As(V) from $P_i$ and can co-adsorb both oxyanions if present. In fact, several metal oxide-based adsorbents featuring iron, copper, magnesium, zirconium, etc. developed in the last decade can be applied for both As(V) and $P_i$ removal (Awual et al., 2011; Kumar et al., 2019; Nicomel et al., 2015; Pan et al., 2009; Pintor et al., 2020; Yang et al., 2020; Zhu et al., 2016). If toxic As(V) is co-recovered with $P_i$, e.g., during ion exchange followed by struvite precipitation, the recovered product will be less palatable for agricultural applications. Long-term agricultural application of $P_i$ fertilizer tainted with As(V) has been identified as one of the main sources of environmental arsenic contamination that can lead to chronic diseases in humans (Hartley et al., 2013; Jayasumana et al., 2015; Mortvedt, 1995).

Bio-inspired adsorbents featuring bacterial PBP may provide a discriminating approach to reversible $P_i$ adsorption while rejecting As(V). PBP occurs naturally in bacteria and is specifically evolved for efficient, selective, and high-affinity binding and transport of $P_i$ (Blank, 2012; Santos-Beneit et al., 2008). The binding mechanisms between $P_i$ and PBP have been extensively studied, and PBP from microorganisms such as *P. fluorescens, Halomonas* sp. GFAJ-1, and *K. variicola* can reportedly discriminate $P_i$ from As(V), even when As(V) is present in excess of 3,000 to 4,000-fold higher concentrations than $P_i$ (Elias et al., 2012). Although it is unlikely that such excess As(V)-to-$P_i$ ratios would be encountered in most wastewaters, a PBP-based reversible $P_i$ adsorbent benefits recovery efforts by efficiently selecting $P_i$ over As(V). Using immobilized PBP (PBP beads or resin), Venkiteshwaran et al. (2018) demonstrated $P_i$ adsorption and subsequent desorption, analogous to ion exchange resins. The PBP beads outperformed other adsorbents reported in the literature with respect to P adsorption kinetics and affinity, and the PBP beads was unaffected by the presence of typical wastewater ions (Cl$^-$, Br$^-$, NO$_2^-$, NO$_3^-$, SO$_4^{2-}$, and HCO$_3$) (Venkiteshwaran et al., 2020). However, $P_i$ adsorption and recovery using PBP beads in the presence of As(V) has not been investigated.

Therefore, the objective of this study was to construct a PBP beads system and analyze its selectivity toward $P_i$ in the presence of As(V) using varying ratios and sequences of addition of $P_i$ and As(V). The purity of the recovered $P_i$ product was also assessed after inducing pH-controlled oxyanion desorption from the PBP beads. This information is critical to evaluating the use of immobilized PBP as an ultra-selective reversible adsorbent This system can be used for $P_i$ recovery in environments in which the primary $P_i$ competitor As(V) is present Materials and Methods PBP Expression and Purification A His-tagged single-cysteine variant (A197C) of the mature *E. coli* pstS PBP (Solscheid et al., 2015) was used in this study. The PBP gene (A197C) overexpression plasmid (plasmid #78198, Addgene, Cambridge, MA, USA) was transformed into BL21(DE3) *E. coli* competent cells, and cultured for pstS protein expression and purification, as described by Venkiteshwaran et al. (2018). The transformed cells were grown in 1-L baffled glass flasks containing LB growth media and incubated at 37° C. with vigorous shaking. The culture was allowed to grow to OD$_{600}$≈0.8 before inducing protein expression using 500 mM isopropyl-β-D-thiogalactopyranoside. After 4-h induction, the culture was centrifuged for 15 min at 4000 g and 4° C. All further steps were conducted at 4° C. The pellets were re-suspended in a buffer containing 10 mM Tris-HCl, 1 mM MgCl$_2$ (hereon, reaction buffer), at pH 8.0 and sonicated 4 times for 30 s at 200 W with a 5 s on/off pulse cycle. The lysate was passed through a 100 mL$_{BV}$ (settled bead volume, where BV=bed volume) Q-Sepharose column (GE Healthcare Bio-Sciences, Pittsburgh, PA, USA). It was then equilibrated with resuspension buffer and eluted using a 100 mL gradient of 0-200 mM NaCl in the resuspension buffer.

PBP Immobilization

The full PBP immobilization protocol is described by Venkiteshwaran et al. (2018). Briefly, the purified PBP was dialyzed and immobilized on N-hydroxy-succinimide (NHS)-activated Sepharose 4 Fast Flow beads in accordance with the manufacturer's instructions (GE Healthcare Bio-Sciences, Pittsburgh, PA, USA). The concentration of the dialyzed PBP was 71±2 µM, as quantified using the Quick Start™ Bradford Protein Assay (Bio-Rad Laboratories Inc., Hercules, CA, USA), using bovine serum albumin as a standard (ThermoFisher Scientific, Waltham, MA, USA). A suspension of 20 mL dialyzed PBP and 10 mL washed NHS beads was mixed at 30 rpm on a Roto-Torque Variable Speed end-over-end rotator (Cole Parmer, IL, USA) for 16 hours at 4° C.

Of the initially loaded PBP (20 mL of 71 µM), >99% was immobilized on the NHS beads, providing a PBP density of 140±0.4 nmoles of PBP per 1 mL NHS beads. Based on 1 mole of PBP adsorbing 1 mole of $P_i$ or As(V) (Brune et al., 1998, 1994; Solscheid et al., 2015), the theoretical adsorption capacity of the NHS beads was 140±0.4 nmoles of $P_i$ or As(V) per mL of NHS beads. The protein coupling density was much lower than the 16-23 µmol-protein/mL-NHS beads reported by the bead manufacturer. Although lower, this coupling density was sufficient to complete the study objectives. In future applications, higher coupling densities could be achieved by using larger batches of PBP.

The NHS beads conjugated with PBP (hereon referred to as PBP beads) were washed with 1V of buffer containing 0.1 M Tris-HCl at pH 8.5. This was followed by three sequential washes with 1V of buffer containing 0.1 M sodium acetate and 0.5 M NaCl at pH 4.5, per manufacturer instructions. Most of the legacy $P_i$ already adsorbed on the PBP during the expression and purification process was subsequently removed by washing the PBP beads with 5$_{BV}$ of reaction buffer at pH 12.5. Washing PBP beads with a pH 12.5 reaction buffer was previously shown to successfully desorb ~90% legacy $P_i$ (Venkiteshwaran et al., 2018). The PBP beads was returned to neutral pH by washing with 5$_{BV}$ of reaction buffer at pH 7 and stored at 4° C. prior to use. A control set of beads was prepared using 20 mL of fresh NHS beads following the same procedure used for the PBP beads, but without PBP addition.

PBP Adsorption and Desorption of $P_i$ and As(V)

Independent Exposure of $P_i$ and As(V) onto PBP Beads

Figure 10:
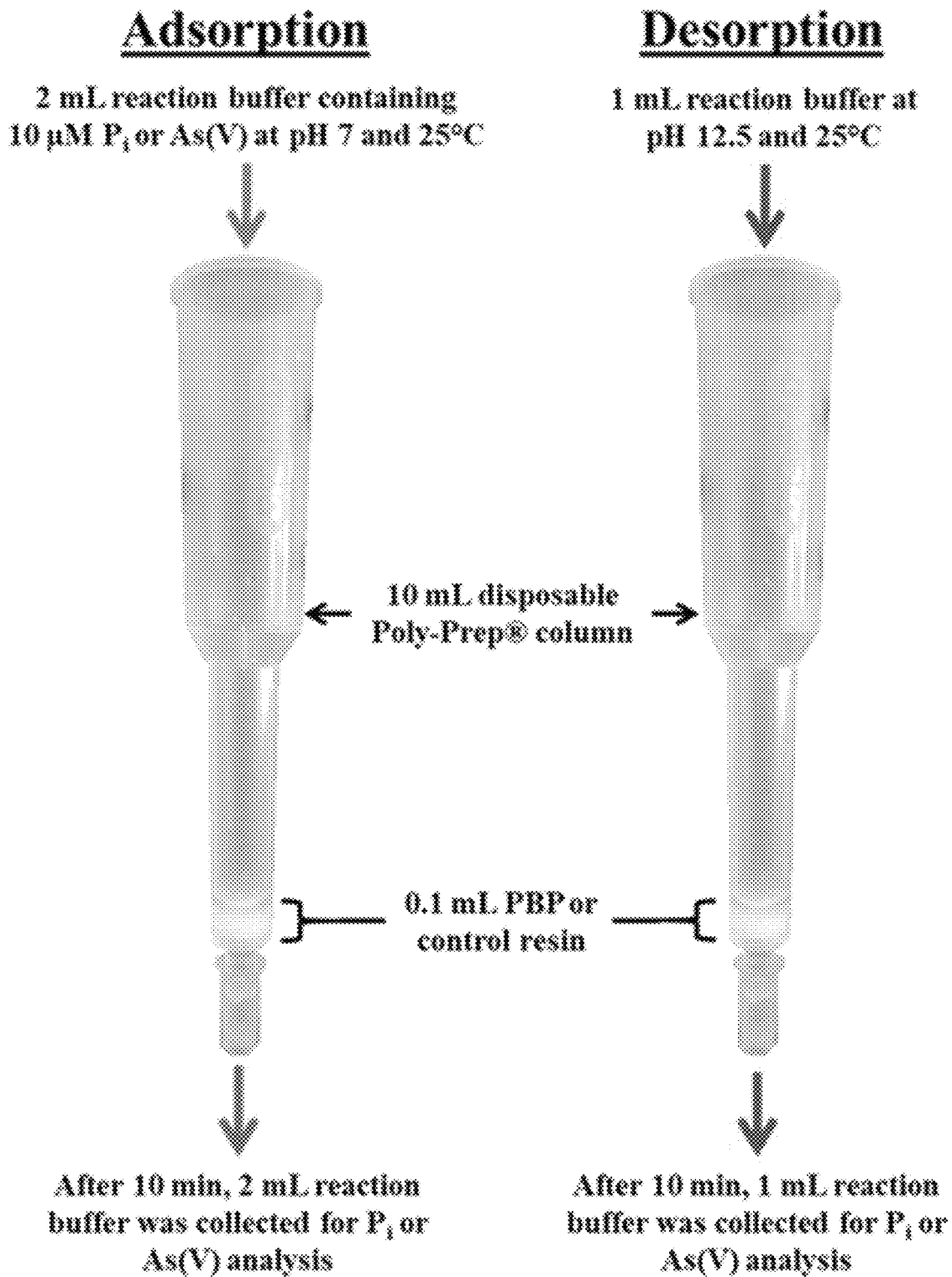
FIG. 10. Experimental set-up investigating the independent exposure of $P_i$ or As(V) onto PBP beads (also referred as PBP resin). Experiments were conducted in triplicate 10 mL disposable Poly-Prep® columns with 0.1 mL of PBP or control beads. Oxyanion adsorption was performed by adding 2 mL ($20_{BV}$) reaction buffer (10 mM Tris-HCl, 1 mM $MgCl_2$) containing 10 µM of $P_i$ or As(V) at pH 7 and 25° C. for 10 min. Desorption of $P_i$ or As(V) from the PBP beads was conducted via addition of 1 mL ($10_{BV}$) of reaction buffer at pH 12.5 and 25° C. for 10 min. A similar experimental set-up was used for investigating sequential and simultaneous exposure of $P_i$ and As(V) to PBP beads.

Adsorption of $P_i$ and As(V) onto PBP beads was initially evaluated independently. All experiments were conducted in triplicate batch tests using 10 mL disposable Poly-Prep® columns (Bio-Rad Laboratories Inc., Hercules, CA, USA) containing 0.1 mL of PBP or control beads. The columns were used to treat 20$_{BV}$ (2 mL) reaction buffer at pH 7 and 25° C. containing 10 µM (20 nmoles) $P_i$ or As(V) (FIG. 10). This concentration exceeded the theoretical capacity of the PBP beads (14.1 nmol PBP/0.1 mL PBP beads) by approximately 1.5× to encourage maximum adsorption. The columns were mixed on a rocker, and the 2 mL reaction buffer was withdrawn after 10 min, which was sufficient time to ensure maximum adsorption onto PBP beads (Venkiteshwaran et al., 2020). The 2 mL buffer was analyzed for $P_i$ or As(V) concentrations.

Desorption of $P_i$ or As(V) from the PBP beads was conducted via addition of $10_{BV}$ (1 mL) of reaction buffer at pH 12.5 and 25° C. (FIG. 10). A 10-min exposure time was used as it was previously shown to be adequate for efficient ion desorption from PBP beads (Venkiteshwaran et al., 2018). The 1 mL reaction buffer was withdrawn and analyzed for concentrations of $P_i$ or As(V) desorbed from the PBP beads. Parallel control experiments were performed using control beads with no PBP to test adsorption on the beads itself.

Sequential Exposure of PBP Beads to P and As(V)

Sequential addition of $P_i$ and As(V) was tested to determine whether fully saturated PBP beads (with all adsorption sites occupied by either $P_i$ or As(V)) would release the initially adsorbed oxyanion species when subsequently exposed to an excess concentration of the competing oxyanion (~1.5-fold excess compared to the theoretical capacity of the PBP beads). The experiments were conducted in triplicate batch tests using 10 mL disposable Poly-Prep® columns with 0.1 mL of PBP beads or control beads. In separate tests, the beads were initially exposed to $P_i$ followed by As(V) or vice versa. Accordingly, 2 mL reaction buffer at pH 7 and 25° C. containing 10 μM of either $P_i$ or As(V) was first added to the beads and allowed to mix for 10 minutes on a rocker table. The 2 mL buffer solution was withdrawn, followed by the addition of 2 mL pH 7 reaction buffer containing 10 μM of the competing anion ($P_i$ or As(V)). After 10 min of mixing on the rocker, the buffer solution was withdrawn. A final desorption wash was performed with 1 mL of pH 12.5 reaction buffer at 25° C. All samples were analyzed for $P_i$ and As(V).

Simultaneous Exposure of PBP Beads to $P_i$ and As(V)

The affinity of PBP beads for As(V) or $P_i$ when the anions were present simultaneously in mixed molar ratios was also evaluated. Triplicate batch tests were performed in 10 mL disposable Poly-Prep® columns with 0.1 mL of PBP or control beads. The beads were exposed to simultaneous additions of 10 μM $P_i$ together with varying As(V) concentrations (0, 1, 5, 10, 15, or 20 μM) in pH 7 reaction buffer at 25° C. and mixed for 10 min on a rocker table. The columns were drained, followed by the final desorption wash with $10_{BV}$ (1 mL) of pH 12.5 reaction buffer for 10 min at 25° C. All samples were assessed for $P_i$ and As(V).

Analytical Methods and Statistical Analysis

All samples collected after the adsorption and desorption steps were tested using a modified ascorbic acid method that allows for simultaneous determination of $P_i$ and As(V) (Carvalho et al., 1998). Using this method, an aliquot of each sample was pretreated using L-cysteine, acetone, and heat, which reduces As(V) to arsenite (As(III)). The reduced As(III) does not interact with molybdenum, thus allowing the determination of $P_i$ in the pretreated sample. The other portion of the sample was not pretreated; thus, the resulting concentration represented the total $P_i$ and As(V). Accordingly, the As(V) concentration was determined by subtracting the pretreated sample from the non-pretreated sample results. The ascorbic acid method was conducted using a HACH DR 3900 spectrophotometer with 2.5 cm light path (APHA, 2012). The minimum detection limit (MDL) was 0.09 μM $P_i$ or As(V), as determined using USEPA (2016) methods.

All PBP beads $P_i$ and As(V) concentration data was normalized to the corresponding control test (identical experiments performed using beads without PBP). The normalized data was also compared to the theoretical $P_i$ or As(V) adsorption capacity of the PBP beads to report the results as nmol $P_i$ or As(V)/nmol PBP. Statistical analysis was performed using one-way ANOVA with Tukey post hoc analysis using GraphPad Prism 6 (GraphPad Software, Inc., La Jolla, CA).

Results and Discussion

Independent Exposure of $P_i$ or As(V) onto PBP Beads

Figure 11:
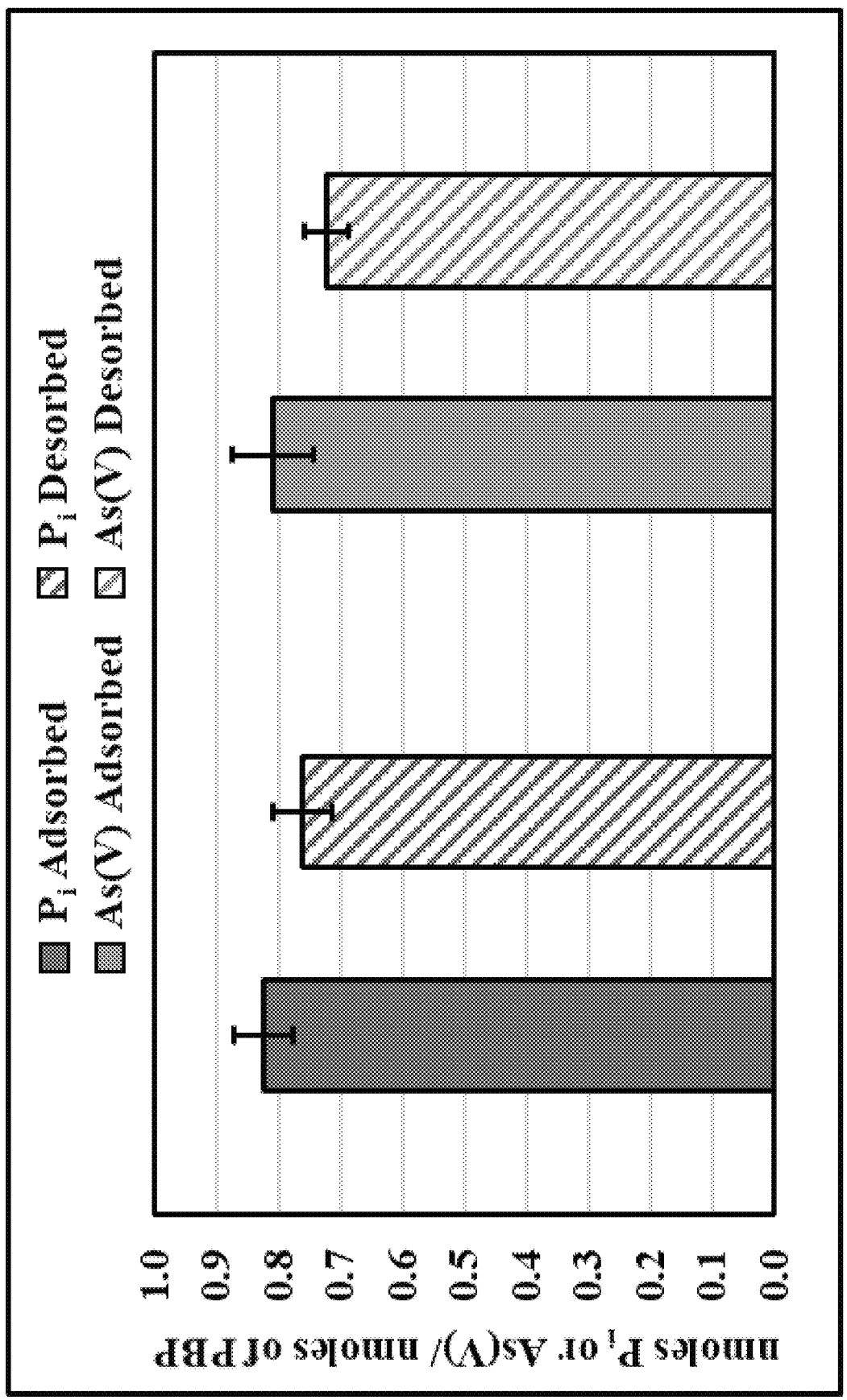
FIG. 11: Normalized adsorption and desorption results from the independent exposure of PBP beads to either $P_i$ or As(V). Experiments were conducted in triplicate 10 mL disposable Poly-Prep® columns with 0.1 mL of PBP or control beads. Oxyanion adsorption was performed by adding 2 mL ($20_{BV}$) reaction buffer (10 mM Tris-HCl, 1 mM $MgCl_2$) containing 10 µM of $P_i$ or As(V) at pH 7 and 25° C. for 10 min. Desorption of $P_i$ or As(V) from the PBP beads was conducted via addition of 1 mL ($10_{BV}$) of reaction buffer at pH 12.5 and 25° C. for 10 min. The error bars represent the standard deviation of triplicate experiments.

The adsorption of $P_i$ or As(V) on PBP beads in the absence of the other competing oxyanion is shown in FIG. 11. The average $P_i$ adsorption on PBP beads was 0.82±0.05 nmol $P_i$/nmol PBP, or 82±5% of the theoretical maximum adsorption capacity, similar to previous reports (Venkiteshwaran et al., 2020, 2018). The average As(V) adsorption was 0.81±0.07 nmol $P_i$/nmol PBP, or 81±7%, which was statistically similar to levels of $P_i$ adsorption (p=0.81). After controlled desorption at pH 12.5, desorption of $P_i$ and As(V) was statistically similar (p=0.4), with approximately 90% of each adsorbed oxyanion recovered. This demonstrated that in the absence of the competing oxyanion, PBP beads was able to adsorb and desorb $P_i$ and As(V) with equal efficiency.

Sequential Exposure of PBP Beads to $P_i$ Followed by As(V) and Vice Versa

Figure 12:
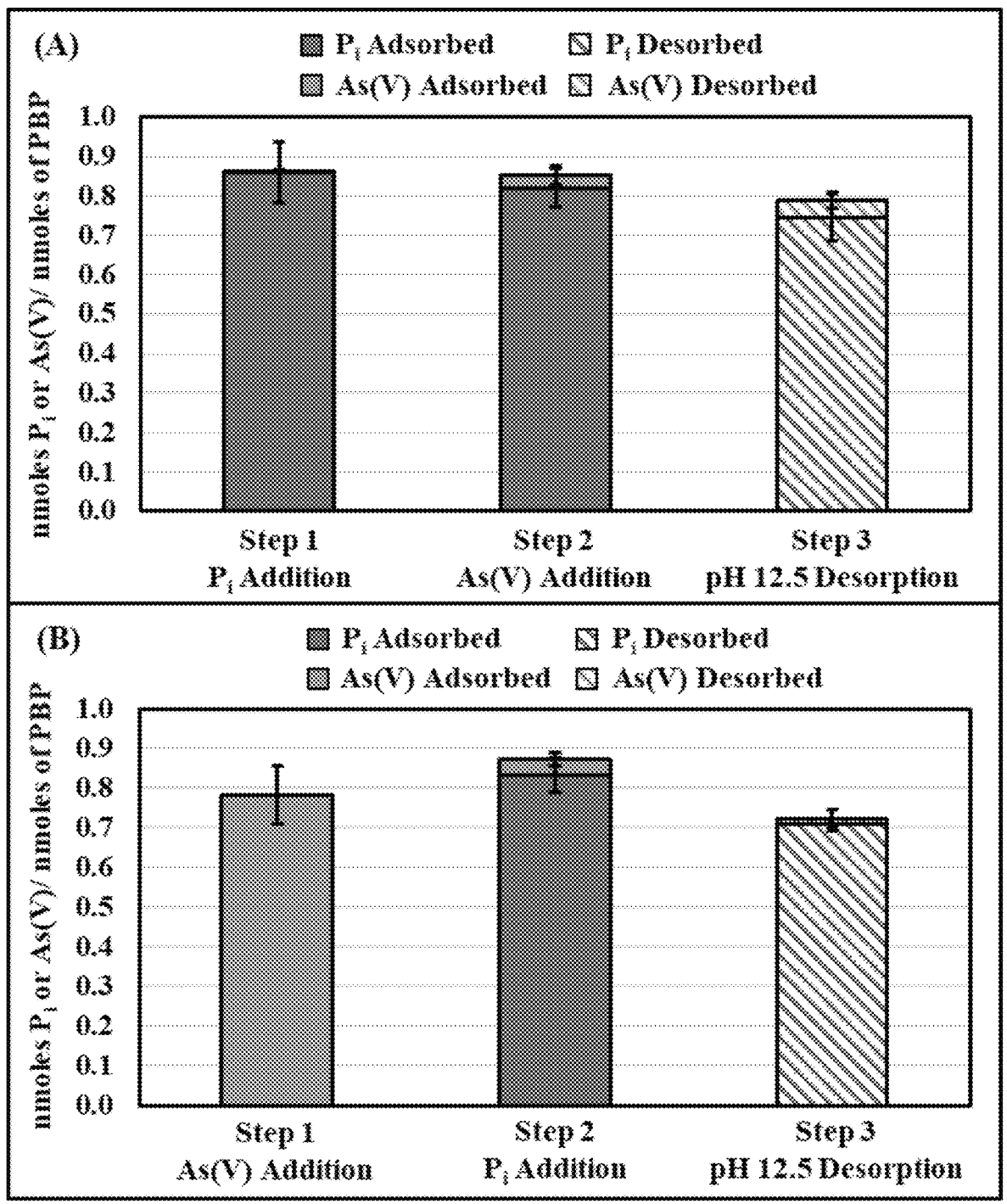
FIG. 12: Results from sequential exposure of PBP beads to $P_i$ or As(V). A) $P_i$ adsorption following (Step 1) addition of $P_i$, (Step 2) addition of As(V), and (Step 3) desorption at pH 12.5. B) As(V) adsorption following (Step 1) addition of As(V), (Step 2) addition of $P_i$, and (Step 3) desorption at pH 12.5. Experiments were conducted in triplicate 10 mL disposable Poly-Prep® columns with 0.1 mL of PBP or control beads. Oxyanion adsorption was performed by adding 2 mL ($20_{BV}$) reaction buffer (10 mM Tris-HCl, 1 mM $MgCl_2$) containing 10 µM of $P_i$ or As(V) at pH 7 and 25° C. for 10 min. Desorption of $P_i$ or As(V) from the PBP beads was conducted via addition of 1 mL ($10_{BV}$) of reaction buffer at pH 12.5 and 25° C. for 10 min. The error bars represent the standard deviation of triplicate experiments.

Once the PBP beads were fully saturated with $P_i$, subsequent exposure to excess As(V) concentrations did not significantly displace the $P_i$ (p=0.57), as more than 95% of the initially adsorbed $P_i$ remained on the PBP beads (FIG. 12A). However, for the PBP beads initially fully saturated with As(V), approximately 95% of the As(V) was replaced by $P_i$ after subsequent exposure to excess $P_i$ concentrations (FIG. 12B). Statistically similar amounts of $P_i$ were adsorbed on the PBP beads after displacing the As(V) compared to when $P_i$ was added to the virgin PBP beads (p=0.94). These results demonstrate that the binding affinity of $P_i$ to PBP beads is much higher than the binding affinity for the closely related oxyanion As(V), thereby minimizing the risk of co-capture of As(V) in the recovered $P_i$ product. Regardless of whether $P_i$ was added first followed by As(V) or vice versa, more than 94% of the recovered product was composed of $P_i$ after the final pH 12.5 desorption step (FIGS. 12A and 12B).

Simultaneous Exposure of PBP Beads to P and As(V)

Figure 13:
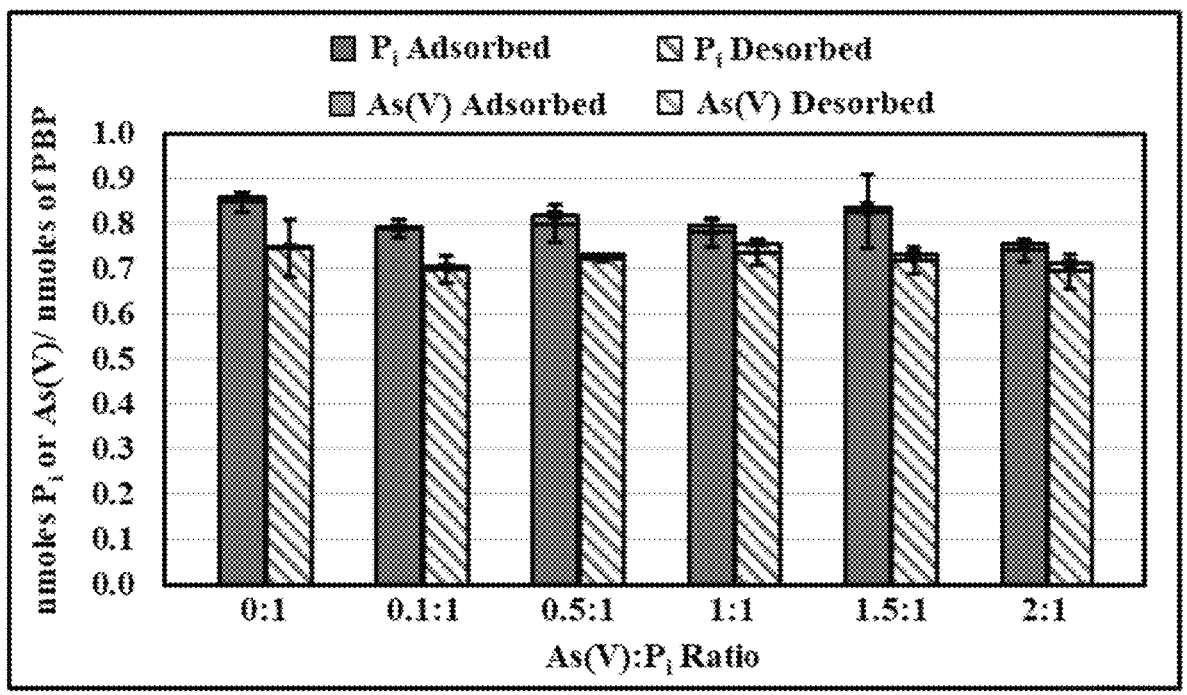
FIG. 13: Adsorption and desorption resulting from the simultaneous exposure of PBP beads to $P_i$ and As(V) at varying As(V):$P_i$ ratios. Experiments were conducted in triplicate 10 mL disposable Poly-Prep® columns with 0.1 mL of PBP or control beads. Oxyanion adsorption was performed by adding 2 mL ($20_{BV}$) reaction buffer (10 mM Tris-HCl, 1 mM $MgCl_2$) containing 10 µM of $P_i$ with varying As(V) concentrations (0, 1, 5, 10, 15, or 20 µM) at pH 7 and 25° C. for 10 min. Oxyanion desorption from the PBP beads was conducted via addition of 1 mL ($10_{BV}$) of reaction buffer at pH 12.5 and 25° C. for 10 min. The error bars represent the standard deviation of triplicate experiment.

Adsorption of $P_i$ and As(V) onto PBP beads resulting from simultaneous exposure to both oxyanions at varying molar ratios is shown in FIG. 13. As the concentration of As(V) increased, there was no statistically significant decrease in $P_i$ adsorption on PBP beads (p=0.12). At the maximum tested As(V):$P_i$ molar ratio of 2, As(V) accounted for less than 3% of the adsorbed oxyanion.

FIG. 13 also shows the composition of As(V) and $P_i$ in the recovered product after the pH 12.5 desorption wash. Under all conditions, the relative fraction of $P_i$ and As(V) in the recovered product matched the composition of the oxyanions adsorbed on the PBP beads, with $P_i$ constituting approximately 98% of the recovered product. Even at an As(V):$P_i$ molar ratio of 2, $P_i$ accounted for 97% of the recovered product. Thus, immobilized PBP can selectivity adsorb $P_i$ and desorb a concentrated, pure $P_i$ product appropriate for agricultural reuse even when As(V) is present in excess in the target wastewater matrix.

How does PBP Discriminate Between $P_i$ and As(V)?

Molecular similarities between As(V) and $P_i$ have made it difficult for current $P_i$ adsorbents to distinguish between the two oxyanions, resulting in lack of $P_i$ selectivity when As(V) is present (Cullen and Reimer, 1989; Marcus, 1997). Bacterial membrane PBPs have evolved to distinguish the subtle structural differences between $P_i$ and As(V), enabling $P_i$ binding (essential for bacterial growth) while preventing the transport of highly toxic As(V) ions inside the cell (Elias et al., 2012; Luecke and Quiocho, 1990). Elias et al. (2012) examined the binding structure of PBP from *P. fluorescens*, which is similar to the *E. coli* PBP used in this study. They reported that PBP-$P_i$ specificity may derive from differences in the chemical bond (via a shared hydrogen atom) between the oxyanions' second oxygen atom (O2) and the oxygen atom in the carboxylate functional group of the aspartate amino acid residue in the PBP binding site. For $P_i$-bound PBP, the hydrogen atom occupies a near-central position between the O2 of the $P_i$ ion and the carboxylate functional group, leading to optimal binding angles between $P_i$ and the aspartate residue. Alternately, the hydrogen atom is asymmetrically located for As(V)-PBP binding, suggesting a weaker interaction, and leading to suboptimal binding angles between As(V) and the aspartate residue. This distortion is the consequence of the longer As—O2 bond than the P—O2 bond and may account for PBP's 500-fold preference for $P_i$ (Elias et al., 2012).

In this study, the PBP beads demonstrated selective $P_i$ adsorption even when As(V) concentration was 2-fold higher than $P_i$. Accordingly, PBP-based adsorbents can exploit PBP's exquisite $P_i$ selectivity, offering the only known $P_i$ adsorbent capable of effectively discriminating against As(V) and thereby recovering a high purity $P_i$ product for reuse.

CONCLUSIONS

This study demonstrated that PBP beads can selectivity adsorb $P_i$ even in cases where As(V) is present at excess levels. The $P_i$ constituted 94% to 98% of the adsorbed oxyanions, as well as the recovered product using PBP beads. This held true even at 2-fold higher molar concentrations of As(V) in comparison to $P_i$. Therefore, PBP beads has the potential to provide a distinct $P_i$ adsorption advantage over existing reversible adsorbents with respect to $P_i$ selectivity. Accordingly, PBP beads can yield a high purity $P_i$ product free of As(V) contamination, which is suitable for agricultural reuse.

REFERENCES

Acelas, N. Y., Martin, B. D., López, D., Jefferson, B., 2015. Selective removal of phosphate from wastewater using hydrated metal oxides dispersed within anionic exchange media. Chemosphere 119, 1353-1360.

American Public Health Association (APHA); American Waterworks Association (AWWA); Water Environment Federation (WEF), 2012. Standard Methods for the Examination of Water and Wastewater, Standard Methods. McGraw-Hill Companies, Inc., New York, NY, USA. ISBN 9780875532356

Awual, M. R., El-Safty, S. A., Jyo, A., 2011. Removal of trace arsenic(V) and phosphate from water by a highly selective ligand exchange adsorbent. J. Environ. Sci. 23, 1947-1954.

Blaney, L. M., Cinar, S., SenGupta, A. K., 2007. Hybrid anion exchanger for trace phosphate removal from water and wastewater. Water Res. 41, 1603-1613.

Blank, L. M., 2012. The cell and P: From cellular function to biotechnological application. Curr. Opin. Biotechnol. 23, 846-851.

Brune, M., Hunter, J. L., Corrie, J. E. T., Webb, M. R., 1994. Direct, Real-Time Measurement of Rapid Inorganic Phosphate Release Using a Novel Fluorescent Probe and Its Application to Actomyosin Subfragment 1 ATPase. Biochemistry 33, 8262-8271.

Brune, M., Hunter, J. L., Howell, S. A., Martin, S. R., Hazlett, T. L, Corrie, J. E. T., Webb, M. R., 1998. Mechanism of inorganic phosphate interaction with phosphate binding protein from *Escherichia coli*. Biochemistry 37, 10370-10380.

Calderon, R. L., Hudgens, E., Le, X. C., Schreinemachers, D., Thomas, D. J., 1999. Excretion of arsenic in urine as a function of exposure to arsenic in drinking water. Environ. Health Perspect. 107, 663-7.

Carvalho, L. H. M., Koe, T. De, Tavares, P. B., 1998. An improved molybdenum blue method for simultaneous determination of inorganic phosphate and arsenate. Ecotoxicol. Environ. Restor. 1, 13-19.

Cortinas, I., Field, J. A., Kopplin, M., Garbarino, J. R., Gandolfi, A. J., Sierra-Alvarez, R., 2006. Anaerobic biotransformation of roxarsone and related N-substituted phenylarsonic acids. Environ. Sci. Technol. 40, 2951-2957.

Cullen, W. R., Reimer, K., 1989. Arsenic Speciation in the Environment Chem. Rev. 89, 713-764.

Elias, M., Wellner, A., Goldin-Azulay, K., Chabriere, E., Vorholt, J. A., Erb, T., Tawfik, D. S., 2012. The molecular basis of phosphate discrimination in arsenate-rich environments. Nature 491, 134-137.

Hartley, T. N., Macdonald, A., McGrath, S. P., Zhao, F., 2013. Historical arsenic contamination of soil due to long-term phosphate fertiliser applications. Environ. Pollut. 180, 259-264.

Jayasumana, C., Fonseka, S., Fernando, A., Jayalath, K., Amarasinghe, M., Siribaddana, S., Gunatilake, S., Paranagama, P., 2015. Phosphate fertilizer is a main source of arsenic in areas affected with chronic kidney disease of unknown etiology in Sri Lanka. Springerplus 4, 1-8.

Kumar, P. S., Korving, L, van Loosdrecht, M. C. M., Witkamp, G., 2019. Adsorption as a technology to achieve ultra-low concentrations of phosphate: Research gaps and economic analysis. Water Res. X.

Luecke, H., Quiocho, F. A., 1990. High specificity of a phosphate transport protein determined by hydrogen bonds. Nature 347, 402-406.

Marcus, Y., 1997. Ion Properties. Marcel Dekker, Inc., New York, Basel., ISBN: 9780824700119

Mayer, B. K., Baker, L. A., Boyer, T. H., Drechsel, P., Gifford, M., Hanjra, M. A., Parameswaran, P., Stoltzfus, J., Westerhoff, P., Rittmann, B. E., 2016. Total Value of Phosphorus Recovery. Environ. Sci. Technol. 50, 6606-6620.

Mayer, B. K., Gerrity, D., Rittmann, B. E., Reisinger, D., Brandt-Williams, S., 2013. Innovative strategies to achieve low total phosphorus concentrations in high water flows. Crit. Rev. Environ. Sci. Technol. 43, 409-441.

Mortvedt, J. J., 1995. Heavy metal contaminants in inorganic and organic fertilizers. Fertil. Res. 43, 55-61.

Nicomel, N. R., Leus, K., Folens, K., Van Der Voort, P., Du Laing, G., 2015. Technologies for Arsenic Removal from Water: Current Status and Future Perspectives. Int. J. Environ. Res. Public Health 13, ijerph13010062.

Pan, Bingjun, Wu, J., Pan, Bingcai, Lv, L., Zhang, W., Xiao, L., Wang, X., Tao, X., Zheng, S., 2009. Development of polymer-based nanosized hydrated ferric oxides (HFOs) for enhanced phosphate removal from waste effluents. Water Res. 43, 4421-4429.

Phyllis2 Database, 2020. Phyllis2—Database for the physico-chemical composition of (treated) lignocellulosic biomass, micro- and macroalgae, various feedstocks for biogas production and biochar.

Pintor, A. M. A., Vieira, B. R. C., Brandaõ, C. C., Boaventura, R. A. R., Botelho, C. M. S., 2020. Complexation mechanisms in arsenic and phosphorus adsorption onto iron-coated cork granulates. J. Environ. Chem. Eng. 8, 104184.

Ronteltap, M., Maurer, M., Gujer, W., 2007. The behaviour of pharmaceuticals and heavy metals during struvite precipitation in urine. Water Res. 41, 1859-1868.

Santos-Beneit, F., Rodríguez-García, A., Franco-Domínguez, E., Martín, J. F., 2008. Phosphate-dependent regulation of the low- and high-affinity transport systems in the model actinomycete Streptomyces coelicolor. Microbiology 154, 2356-2370.

SenGupta, A., Cumbal, L. H., 2007. Hybrid anion exchanger for selective removal of contaminating ligands from fluids and method of manufacture thereof. US20050156136A1.

Solscheid, C., Kunzelmann, S., Davis, C. T., Hunter, J. L., Nofer, A., Webb, M. R., 2015. Development of a Reagent-less Biosensor for Inorganic Phosphate, Applicable over a Wide Concentration Range. Biochemistry 54, 5054-5062.

USEPA, 2016. Office of Water Definition and Procedure for the Determination of the Method Detection Limit, Revision 2. United States Environ. Prot. Agency, Off. Water. URL: www.epa.gov/cwa-methods/procedures-detection-and-quantitation-documents Uysal, A., Yilmazel, Y. D., Demirer, G. N., 2010. The determination of fertilizer quality of the formed struvite from effluent of a sewage sludge anaerobic digester. J. Hazard. Mater. 181, 248-254.

Venkiteshwaran, K., Pokhrel, N., Hussein, F., Antony, E., Mayer, B. K., 2018. Phosphate removal and recovery using immobilized phosphate binding proteins. Water Res. X 1, 100003.

Venkiteshwaran, K., Wells, E., Mayer, B. K., 2020. Kinetics, affinity, thermodynamics, and selectivity of phosphate removal using immobilized phosphate-binding proteins. Environ. Sci. Technol.

Yang, C. H., Chang, J. S., Lee, D., 2020. Covalent organic framework EB-COF:Br as adsorbent for phosphorus (V) or arsenic (V) removal from nearly neutral waters. Chemosphere 253, 126736.

You, X., Guaya, D., Farran, A., Valderrama, C., Cortina, J. L., 2016. Phosphate removal from aqueous solution using a hybrid impregnated polymeric sorbent containing hydrated ferric oxide (HFO). J. Chem. Technol. Biotechnol. 91, 693-704.

Zhu, N., Yan, T., Qiao, J., Cao, H., 2016. Adsorption of arsenic, phosphorus and chromium by bismuth impregnated biochar: Adsorption mechanism and depleted adsorbent utilization. Chemosphere 164, 32-40.

The invention claimed is:

1. A method of concentrating and recovering phosphate from a sample, the method comprising:
   (a) exposing a liquid sample to immobilized phosphate binding protein (PBP) for a sufficient amount of time to bind phosphate to the immobilized PBP within the sample; and
   (b) contacting the immobilized PBP with a desorption solution having a pH of 11 or greater to desorb the phosphate from the immobilized PBP, wherein the phosphate is concentrated with the desorption solution.

2. The method of claim 1, wherein the method further comprises after (a) a wash step with a washing solution at a neutral pH to remove non-specific binding of other ions in the water.

3. The method of claim 1, wherein the PBP is immobilized on resins or a membrane or expressed on the surface of a bacteria.

4. The method of claim 3, wherein the PBP is expressed on a bacteria, and the bacteria is *E. coli*.

5. The method of claim 1, wherein the PBP is PstS.

6. The method of claim 1, wherein the volume of the desorption solution can be about 2 to 10 times less than the raw liquid sample.

7. The method of claim 1, wherein the method further comprises:
   (c) reusing the immobilized PBP by
       (i) washing the immobilized PBP with a washing solution at a neutral pH between pH 6.8-7.5,
       (ii) re-exposing the immobilized PBP with a second sample,
       (iii) desorbing the phosphate from the immobilized PBP by exposing the immobilized PBP to desorption solution of pH of 12 or higher, and
       (iv) recovering the phosphate in the desorption solution.

8. The method of claim 1, wherein the volume of the desorption solution is sufficient to concentrate the phosphate to a reliably quantifiable level.

9. The method of claim 8, wherein the concentration of the phosphate in the sample before step (a) is from about 0-50 µg/L.

10. The method of claim 1, wherein the method further comprises detecting the phosphate within the desorption solution.

11. The method of claim 1, wherein the water sample is an environmental water sample or wastewater sample.

12. The method of claim 11, the environmental water is river water, lake water, pond water, stream water or creek water, or the wastewater sample is domestic wastewater or agricultural wastewater.

13. The method of claim 1, wherein the desorption solution has a pH of 12 or greater.

14. The method of claim 13, wherein the desorption solution has a pH of 12.5 or greater, and wherein at least 80% of the phosphate is released from the PBP.

15. A method of concentrating low levels of phosphate in a sample, the method comprising:
   (a) exposing a liquid sample to immobilized phosphate binding protein (PBP) for a sufficient amount of time to bind phosphate to the immobilized PBP within the sample; and
   (b) desorbing the phosphate from the immobilized PBP by contacting the immobilized PBP with a desorption solution having a pH of 11 or greater wherein the volume of the desorption solution is at least half of the starting sample volume and the phosphate is concentrated to a detectable level.

16. The method of claim 15, wherein the desorption solution of step (b) is neutralized to a neutral pH with the addition of an acid.

17. The method of claim 16, wherein (a) the PBP is immobilized on resins, a membrane or bacteria.

18. The method of claim 15, wherein the PBP is PstS.

19. The method of claim 15, wherein the concentration of the phosphate in the sample before step (a) is from about 0-50 µg/L.

20. The method of claim 15, wherein the wherein the desorption solution has a pH of 12 or greater.

* * * * *

UNITED STATES PATENT AND TRADEMARK OFFICE
CERTIFICATE OF CORRECTION

PATENT NO. : 12,037,265 B2
APPLICATION NO. : 17/153471
DATED : July 16, 2024
INVENTOR(S) : Brooke Mayer et al.

Page 1 of 2

It is certified that error appears in the above-identified patent and that said Letters Patent is hereby corrected as shown below:

In the Specification

Column 3, Line 24, "IIlustration" should be --Illustration--.

Column 6, Line 31, "POAG82" should be --P0AG82--.

Column 6, Line 41, "NCB" should be --NCBI--.

Column 6, Line 43, "POAG82" should be --P0AG82--.

Column 10, Line 14, "PTG" should be --IPTG--.

Column 11, Line 35, "As(II)" should be --(As(III)--.

Column 14, Line 57, "IV" should be --$1_{BV}$--.

Column 14, Line 59, "IV" should be --$1_{BV}$--.

Column 15, Line 3, "IV" should be --$1_{BV}$--.

Column 16, Line 22, "11.84" should be --11.8±4--.

Column 16, Line 23, "248%" should be --24±8%--.

Column 16, Line 41, "7.92" should be --7.9±2--.

Column 17, Line 25, "715%" should be --71±5%--.

Column 18, Line 17, "NaHC$_3$" should be --NaHCO$_3$--.

Signed and Sealed this
Tenth Day of September, 2024

Katherine Kelly Vidal
*Director of the United States Patent and Trademark Office*

CERTIFICATE OF CORRECTION (continued)
U.S. Pat. No. 12,037,265 B2

Column 18, Line 21, "$MgC_2$" should be --$MgCl_2$--.

Column 22, Line 43, "IV" should be --$1_{BV}$--.

Column 22, Line 45, "IV" should be --$1_{BV}$--.

SEQUENCE LISTING

```
<160> NUMBER OF SEQ ID NOS: 11

<210> SEQ ID NO 1
<211> LENGTH: 346
<212> TYPE: PRT
<213> ORGANISM: Escherichia coli
<220> FEATURE:
<221> NAME/KEY: MISC_FEATURE
<222> LOCATION: (1)..(25)
<223> OTHER INFORMATION: Signal peptide
<220> FEATURE:
<221> NAME/KEY: MISC_FEATURE
<222> LOCATION: (1)..(346)
<223> OTHER INFORMATION: wild type PBP from the E. coli K-12 strain

<400> SEQUENCE: 1

Met Lys Val Met Arg Thr Thr Val Ala Thr Val Val Ala Ala Thr Leu
1               5                   10                  15

Ser Met Ser Ala Phe Ser Val Phe Ala Glu Ala Ser Leu Thr Gly Ala
            20                  25                  30

Gly Ala Thr Phe Pro Ala Pro Val Tyr Ala Lys Trp Ala Asp Thr Tyr
        35                  40                  45

Gln Lys Glu Thr Gly Asn Lys Val Asn Tyr Gln Gly Ile Gly Ser Ser
    50                  55                  60

Gly Gly Val Lys Gln Ile Ile Ala Asn Thr Val Asp Phe Gly Ala Ser
65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
            100                 105                 110

Leu Lys Ser Gly Glu Leu Val Leu Asp Gly Lys Thr Leu Gly Asp Ile
```

```
                115                 120                 125
Tyr Leu Gly Lys Ile Lys Lys Trp Asp Asp Glu Ala Ile Ala Lys Leu
            130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
            180                 185                 190

Trp Pro Ile Gly Leu Gly Gly Lys Gly Asn Asp Gly Ile Ala Ala Phe
                195                 200                 205

Val Gln Arg Leu Pro Gly Ala Ile Gly Tyr Val Glu Tyr Ala Tyr Ala
            210                 215                 220

Lys Gln Asn Asn Leu Ala Tyr Thr Lys Leu Ile Ser Ala Asp Gly Lys
225                 230                 235                 240

Pro Val Ser Pro Thr Glu Glu Asn Phe Ala Asn Ala Ala Lys Gly Ala
                245                 250                 255

Asp Trp Ser Lys Thr Phe Ala Gln Asp Leu Thr Asn Gln Lys Gly Glu
            260                 265                 270

Asp Ala Trp Pro Ile Thr Ser Thr Phe Ile Leu Ile His Lys Asp
                275                 280                 285

Gln Lys Lys Pro Glu Gln Gly Thr Glu Val Leu Lys Phe Phe Asp Trp
            290                 295                 300

Ala Tyr Lys Thr Gly Ala Lys Gln Ala Asn Asp Leu Asp Tyr Ala Ser
305                 310                 315                 320

Leu Pro Asp Ser Val Val Glu Gln Val Arg Ala Ala Trp Lys Thr Asn
                325                 330                 335

Ile Lys Asp Ser Ser Gly Lys Pro Leu Tyr
                340                 345

<210> SEQ ID NO 2
<211> LENGTH: 322
<212> TYPE: PRT
<213> ORGANISM: Artificial Sequence
<220> FEATURE:
<223> OTHER INFORMATION: PBP from E. coli K-12 strain (SEQ ID NO: 1)
      with the signal peptide removed and replaced with start codon
      methionine (M)

<400> SEQUENCE: 2

Met Glu Ala Ser Leu Thr Gly Ala Gly Ala Thr Phe Pro Ala Pro Val
1               5                   10                  15

Tyr Ala Lys Trp Ala Asp Thr Tyr Gln Lys Glu Thr Gly Asn Lys Val
                20                  25                  30

Asn Tyr Gln Gly Ile Gly Ser Ser Gly Val Lys Gln Ile Ile Ala
                35                  40                  45

Asn Thr Val Asp Phe Gly Ala Ser Asp Ala Pro Leu Ser Asp Glu Lys
            50                  55                  60

Leu Ala Gln Glu Gly Leu Phe Gln Phe Pro Thr Val Ile Gly Gly Val
65              70                  75                  80

Val Leu Ala Val Asn Ile Pro Gly Leu Lys Ser Gly Glu Leu Val Leu
                85                  90                  95

Asp Gly Lys Thr Leu Gly Asp Ile Tyr Leu Gly Lys Ile Lys Lys Trp
            100                 105                 110

Asp Asp Glu Ala Ile Ala Lys Leu Asn Pro Gly Leu Lys Leu Pro Ser
            115                 120                 125
```

```
Gln Asn Ile Ala Val Val Arg Arg Ala Asp Gly Ser Gly Thr Ser Phe
    130                 135                 140
Val Phe Thr Ser Tyr Leu Ala Lys Val Asn Glu Glu Trp Lys Asn Asn
145                 150                 155                 160
Val Gly Thr Gly Ser Thr Val Lys Trp Pro Ile Gly Leu Gly Gly Lys
                165                 170                 175
Gly Asn Asp Gly Ile Ala Ala Phe Val Gln Arg Leu Pro Gly Ala Ile
            180                 185                 190
Gly Tyr Val Glu Tyr Ala Tyr Ala Lys Gln Asn Asn Leu Ala Tyr Thr
        195                 200                 205
Lys Leu Ile Ser Ala Asp Gly Lys Pro Val Ser Pro Thr Glu Glu Asn
210                 215                 220
Phe Ala Asn Ala Ala Lys Gly Ala Asp Trp Ser Lys Thr Phe Ala Gln
225                 230                 235                 240
Asp Leu Thr Asn Gln Lys Gly Glu Asp Ala Trp Pro Ile Thr Ser Thr
                245                 250                 255
Thr Phe Ile Leu Ile His Lys Asp Gln Lys Lys Pro Glu Gln Gly Thr
            260                 265                 270
Glu Val Leu Lys Phe Phe Asp Trp Ala Tyr Lys Thr Gly Ala Lys Gln
        275                 280                 285
Ala Asn Asp Leu Asp Tyr Ala Ser Leu Pro Asp Ser Val Val Glu Gln
    290                 295                 300
Val Arg Ala Ala Trp Lys Thr Asn Ile Lys Asp Ser Ser Gly Lys Pro
305                 310                 315                 320
Leu Tyr

<210> SEQ ID NO 3
<211> LENGTH: 966
<212> TYPE: DNA
<213> ORGANISM: Artificial Sequence
<220> FEATURE:
<223> OTHER INFORMATION: PBP from E. coli K-12 strain (SEQ ID NO: 1)
      with the signal peptide removed and replaced with start codon
      methionine (M)

<400> SEQUENCE: 3
atggaagcaa gcctgacagg tgcaggtgca accttccctg cgccggtgta tgccaaatgg     60
gctgacactt accagaaaga aaccggtaat aaagttaact accagggtat cggttcttcc    120
ggtggcgtaa aacagattat cgctaatacc gttgattttg gtgcctctga cgcgccgctg    180
tctgacgaaa aactggctca ggaaggtctg ttccagttcc cgaccgtgat ggcggcgtg    240 gtgctggcgg ttaacattcc agggctgaag tctggcgaac tggtgctgga tggtaaaacc    300
ctcggcgaca tctacctggg caaaatcaag aagtgggatg atgaagccat cgccaaactg    360
aatccgggtc tgaaactgcc ttcacaaaac attgctgtag tacgccgcgc agatggctcc    420
gggacttcct tcgtcttcac cagctacctg gcgaaagtga acgaagagtg gaaaaacaac    480
gttggtactg gctctaccgt aaaatggccg atcggtctgg gcggtaaagg taacgacggt    540
atcgccgcgt tcgttcagcg tctgccgggt gcaattggtt atgttgaata tgcttacgcg    600
aagcagaaca acctggcgta caccaaactg atctccgctg atggtaaacc ggttagtccg    660
accgaagaaa acttcgctaa tgcagcaaaa ggtgcagact ggagcaaaac cttcgctcag    720
gatctgacca accagaaagg cgaagatgca tggcctatta cctctaccac gttcattctg    780
atccacaaag atcagaagaa accagaacaa ggcacagaag tgctgaaatt cttcgactgg    840
```

```
gcgtacaaaa ccggggctaa acaggcgaac gacctggatt acgccagcct gccggatagt    900
gtagttgaac aggttcgcgc tgcgtggaag accaatatta aagacagtag cggtaagccg    960
ctgtac                                                                966
```

<210> SEQ ID NO 4
<211> LENGTH: 322
<212> TYPE: PRT
<213> ORGANISM: Artificial Sequence
<220> FEATURE:
<223> OTHER INFORMATION: PBP from E. coli K-12 strain with the signal
      peptide removed and replaced with methionine (M), and alanine (A)
      in position 197 replaced with cysteine (C)

<400> SEQUENCE: 4

```
Met Glu Ala Ser Leu Thr Gly Ala Gly Ala Thr Phe Pro Ala Pro Val
1               5                   10                  15

Tyr Ala Lys Trp Ala Asp Thr Tyr Gln Lys Glu Thr Gly Asn Lys Val
            20                  25                  30

Asn Tyr Gln Gly Ile Gly Ser Ser Gly Gly Val Lys Gln Ile Ile Ala
        35                  40                  45

Asn Thr Val Asp Phe Gly Ala Ser Asp Ala Pro Leu Ser Asp Glu Lys
    50                  55                  60

Leu Ala Gln Glu Gly Leu Phe Gln Phe Pro Thr Val Ile Gly Gly Val
65                  70                  75                  80

Val Leu Ala Val Asn Ile Pro Gly Leu Lys Ser Gly Glu Leu Val Leu
                85                  90                  95

Asp Gly Lys Thr Leu Gly Asp Ile Tyr Leu Gly Lys Ile Lys Lys Trp
            100                 105                 110

Asp Asp Glu Ala Ile Ala Lys Leu Asn Pro Gly Leu Lys Leu Pro Ser
        115                 120                 125

Gln Asn Ile Ala Val Val Arg Arg Ala Asp Gly Ser Gly Thr Ser Phe
    130                 135                 140

Val Phe Thr Ser Tyr Leu Ala Lys Val Asn Glu Glu Trp Lys Asn Asn
145                 150                 155                 160

Val Gly Thr Gly Ser Thr Val Lys Trp Pro Ile Gly Leu Gly Gly Lys
                165                 170                 175

Gly Asn Asp Gly Ile Ala Ala Phe Val Gln Arg Leu Pro Gly Ala Ile
            180                 185                 190

Gly Tyr Val Glu Tyr Cys Tyr Ala Lys Gln Asn Asn Leu Ala Tyr Thr
        195                 200                 205

Lys Leu Ile Ser Ala Asp Gly Lys Pro Val Ser Pro Thr Glu Glu Asn
    210                 215                 220

Phe Ala Asn Ala Ala Lys Gly Ala Asp Trp Ser Lys Thr Phe Ala Gln
225                 230                 235                 240

Asp Leu Thr Asn Gln Lys Gly Glu Asp Ala Trp Pro Ile Thr Ser Thr
                245                 250                 255

Thr Phe Ile Leu Ile His Lys Asp Gln Lys Pro Glu Gln Gly Thr
            260                 265                 270

Glu Val Leu Lys Phe Phe Asp Trp Ala Tyr Lys Thr Gly Ala Lys Gln
        275                 280                 285

Ala Asn Asp Leu Asp Tyr Ala Ser Leu Pro Asp Ser Val Val Glu Gln
    290                 295                 300

Val Arg Ala Ala Trp Lys Thr Asn Ile Lys Asp Ser Ser Gly Lys Pro
305                 310                 315                 320

Leu Tyr
```

<210> SEQ ID NO 5
<211> LENGTH: 966
<212> TYPE: DNA
<213> ORGANISM: Artificial Sequence
<220> FEATURE:
<223> OTHER INFORMATION: PBP from E. coli K-12 strain with the signal
      peptide removed and replaced with methionine (M), and alanine (A)
      in position 197 replaced with cysteine (C)

<400> SEQUENCE: 5

```
atggaagcaa gcctgacagg tgcaggtgca accttccctg cgccggtgta tgccaaatgg     60
gctgacactt accagaaaga aaccggtaat aaagttaact accagggtat cggttcttcc    120
ggtggcgtaa acagattat cgctaatacc gttgattttg gtgcctctga cgcgccgctg    180
tctgacgaaa aactggctca ggaaggtctg ttccagttcc cgaccgtgat tggcggcgtg    240
gtgctggcgg ttaacattcc agggctgaag tctggcgaac tggtgctgga tggtaaaacc    300
ctcggcgaca tctacctggg caaaatcaag aagtgggatg atgaagccat cgccaaactg    360
aatccgggtc tgaaactgcc ttcacaaaac attgctgtag tacgccgcgc agatggctcc    420
gggacttcct tcgtcttcac cagctacctg gcgaaagtga cgaagagtg gaaaaacaac    480
gttggtactg gctctaccgt aaaatggccg atcggtctgg gcggtaaagg taacgacggt    540
atcgccgcgt tcgttcagcg tctgccgggt gcaattggtt atgttgaata ttgttacgcg    600
aagcagaaca acctggcgta caccaaactg atctccgctg atggtaaacc ggttagtccg    660
accgaagaaa acttcgctaa tgcagcaaaa ggtgcagact ggagcaaaac cttcgctcag    720
gatctgacca ccagaaagg cgaagatgca tggcctatta cctctaccac gttcattctg    780
atccacaaag atcagaagaa accagaacaa ggcacagaag tgctgaaatt cttcgactgg    840
gcgtacaaaa ccggggctaa acaggcgaac gacctggatt acgccagcct gccggatagt    900
gtagttgaac aggttcgcgc tgcgtggaag accaatatta agacagtag cggtaagccg    960
ctgtac                                                               966
```

<210> SEQ ID NO 6
<211> LENGTH: 321
<212> TYPE: PRT
<213> ORGANISM: Escherichia coli
<220> FEATURE:
<221> NAME/KEY: MISC_FEATURE
<222> LOCATION: (1)..(346)
<223> OTHER INFORMATION: PBP from E. coli K-12 strain without the signal
      sequence

<400> SEQUENCE: 6

Glu Ala Ser Leu Thr Gly Ala Gly Ala Thr Phe Pro Ala Pro Val Tyr
1               5                   10                  15

Ala Lys Trp Ala Asp Thr Tyr Gln Lys Glu Thr Gly Asn Lys Val Asn
                20                  25                  30

Tyr Gln Gly Ile Gly Ser Ser Gly Gly Val Lys Gln Ile Ile Ala Asn
            35                  40                  45

Thr Val Asp Phe Gly Ala Ser Asp Ala Pro Leu Ser Asp Glu Lys Leu
        50                  55                  60

Ala Gln Glu Gly Leu Phe Gln Phe Pro Thr Val Ile Gly Gly Val Val
65                  70                  75                  80

Leu Ala Val Asn Ile Pro Gly Leu Lys Ser Gly Glu Leu Val Leu Asp
                85                  90                  95

Gly Lys Thr Leu Gly Asp Ile Tyr Leu Gly Lys Ile Lys Lys Trp Asp

```
            100                 105                 110
Asp Glu Ala Ile Ala Lys Leu Asn Pro Gly Leu Lys Leu Pro Ser Gln
        115                 120                 125
Asn Ile Ala Val Val Arg Arg Ala Asp Gly Ser Gly Thr Ser Phe Val
        130                 135                 140
Phe Thr Ser Tyr Leu Ala Lys Val Asn Glu Glu Trp Lys Asn Asn Val
145                 150                 155                 160
Gly Thr Gly Ser Thr Val Lys Trp Pro Ile Gly Leu Gly Gly Lys Gly
                165                 170                 175
Asn Asp Gly Ile Ala Ala Phe Val Gln Arg Leu Pro Gly Ala Ile Gly
                180                 185                 190
Tyr Val Glu Tyr Ala Tyr Ala Lys Gln Asn Asn Leu Ala Tyr Thr Lys
                195                 200                 205
Leu Ile Ser Ala Asp Gly Lys Pro Val Ser Pro Thr Glu Glu Asn Phe
        210                 215                 220
Ala Asn Ala Ala Lys Gly Ala Asp Trp Ser Lys Thr Phe Ala Gln Asp
225                 230                 235                 240
Leu Thr Asn Gln Lys Gly Glu Asp Ala Trp Pro Ile Thr Ser Thr Thr
                245                 250                 255
Phe Ile Leu Ile His Lys Asp Gln Lys Lys Pro Glu Gln Gly Thr Glu
                260                 265                 270
Val Leu Lys Phe Phe Asp Trp Ala Tyr Lys Thr Gly Ala Lys Gln Ala
                275                 280                 285
Asn Asp Leu Asp Tyr Ala Ser Leu Pro Asp Ser Val Val Glu Gln Val
        290                 295                 300
Arg Ala Ala Trp Lys Thr Asn Ile Lys Asp Ser Ser Gly Lys Pro Leu
305                 310                 315                 320
Tyr

<210> SEQ ID NO 7
<211> LENGTH: 346
<212> TYPE: PRT
<213> ORGANISM: Shigella flexneri
<220> FEATURE:
<221> NAME/KEY: MISC_FEATURE
<222> LOCATION: (1)..(346)
<223> OTHER INFORMATION: PBP from Shigella flexneri 301 strain

<400> SEQUENCE: 7

Met Lys Val Met Arg Thr Thr Val Ala Thr Val Ala Ala Thr Leu
1               5                   10                  15
Ser Met Ser Ala Phe Ser Val Phe Ala Glu Ala Ser Leu Thr Gly Ala
                20                  25                  30
Gly Ala Thr Phe Pro Ala Pro Val Tyr Ala Lys Trp Ala Asp Thr Tyr
            35                  40                  45
Gln Lys Glu Thr Gly Asn Lys Val Asn Tyr Gln Gly Ile Gly Ser Ser
        50                  55                  60
Gly Gly Val Lys Gln Ile Ile Ala Asn Thr Val Asp Phe Gly Ala Ser
65                  70                  75                  80
Asp Ala Pro Leu Ser Asp Glu Lys Leu Ala Gln Glu Gly Leu Phe Gln
                85                  90                  95
Phe Pro Thr Val Ile Gly Gly Val Val Leu Ala Val Asn Ile Pro Gly
                100                 105                 110
Leu Lys Ser Gly Glu Leu Val Leu Asp Gly Lys Thr Leu Gly Asp Ile
        115                 120                 125
```

```
Tyr Leu Gly Lys Ile Lys Lys Trp Asp Asp Glu Ala Ile Ala Lys Leu
            130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
                180                 185                 190

Trp Pro Ile Gly Leu Gly Gly Lys Gly Asn Asp Gly Ile Ala Ala Phe
                195                 200                 205

Val Gln Arg Leu Pro Gly Ala Ile Gly Tyr Val Glu Tyr Ala Tyr Ala
            210                 215                 220

Lys Gln Asn Asn Leu Ala Tyr Thr Lys Leu Ile Ser Ala Asp Gly Lys
225                 230                 235                 240

Pro Val Ser Pro Thr Glu Asn Phe Ala Asn Ala Ala Lys Gly Ala
                245                 250                 255

Asp Trp Ser Lys Thr Phe Ala Gln Asp Leu Thr Asn Gln Lys Gly Glu
                260                 265                 270

Asp Ala Trp Pro Ile Thr Ser Thr Thr Phe Ile Leu Ile His Lys Asp
            275                 280                 285

Gln Lys Lys Pro Glu Gln Gly Thr Glu Val Leu Lys Phe Phe Asp Trp
290                 295                 300

Ala Tyr Lys Thr Gly Ala Lys Gln Ala Asn Asp Leu Asp Tyr Ala Ser
305                 310                 315                 320

Leu Pro Asp Ser Val Val Glu Gln Val Arg Ala Ala Trp Lys Thr Asn
                325                 330                 335

Ile Lys Asp Ser Ser Gly Lys Pro Leu Tyr
                340                 345

<210> SEQ ID NO 8
<211> LENGTH: 1665
<212> TYPE: DNA
<213> ORGANISM: Artificial Sequence
<220> FEATURE:
<223> OTHER INFORMATION: Anchor protein (ice nucleation protein inaK-N)
      and target PBP (pstS) inserted into a plasmid for surface
      expression

<400> SEQUENCE: 8
gacagcaaat gggtcgggat ctgtacgacg atgacgataa ggatcctgct gtaatgactc      60
tcgacaaggc gttggtgctg cgtacctgtg caaataacat ggccgatcac tgcggcctta     120
tatggcccgc gtccggcacg gtggaatcca gatactggca gtcaaccagg cggcatgaga     180
atggtctggt cggtttactg tggggcgctg gaaccagcgc ttttctaagc gtgcatgccg     240
atgctcgatg gattgtctgt gaagttgccg ttgcagacat catcagtctg gaagagccgg     300
gaatggtcaa gtttccgcgg gccgaggtgg ttcatgtcgg cgacaggatc agcgcgtcac     360
acttcatttc ggcacgtcag gccgaccctg cgtcaacgtc aacgtcaacg tcaacgtcaa     420
cgttaacgcc aatgcctacg gccatacccg cgccatgcc tgcggtagca agtgtcacgt      480
taccggtggc cgaacaggcc cgtcatgaag tgttcgatgt cgcgtcggtc agcgcggctg     540 ccgcccagt aaacaccctg ccggtgacga cgccgcagaa tatgaaagtt atgcgtacca      600
ccgtcgcaac tgttgtcgcc gcgaccttat cgatgagtgc tttctctgtg tttgcagaag     660
caagcctgac aggtgcaggt gcaaccttcc ctgcgccggt gtatgccaaa tgggctgaca     720
cttaccagaa agaaaccggt aataaagtta actaccaggg tatcggttct tccggtggcg     780
```

```
taaaacagat tatcgctaat accgttgatt ttggtgcctc tgacgcgccg ctgtctgacg    840
aaaaactggc tcaggaaggt ctgttccagt tcccgaccgt gattggcggc gtggtggcgg    900
ttaacattcc agggctgaag tctggcgaac tggtgctgga tggtaaaacc ctcggcgaca    960
tctacctggg caaaatcaag aagtgggatg atgaagccat cgccaaactg aatccgggtc   1020
tgaaactgcc ttcacaaaac attgctgtag tacgccgcgc agatggctcc gggacttcct   1080
tcgtcttcac cagctacctg gcgaaagtga acgaagagtg gaaaaacaac gttggtactg   1140
gctctaccgt aaaatggccg atcggtctgg cggtaaagg taacgacggt atcgccgcgt   1200
tcgttcagcg tctgccgggt gcaattggtt atgttgaata tgcttacgcg aagcagaaca   1260
acctggcgta caccaaactg atctccgctg atggtaaacc ggttagtccg accgaagaaa   1320
acttcgctaa tgcagcaaaa ggtgcagact ggagcaaaac cttcgctcag gatctgacca   1380
accagaaagg cgaagatgca tggcctatta cctctaccac gttcattctg atccacaaag   1440
atcagaagaa accagaacaa ggcacagaag tgctgaaatt cttcgactgg gcgtacaaaa   1500
ccggggctaa acaggcgaac gacctggatt acgccagcct gccggatagt gtagttgaac   1560
aggttcgcgc tgcgtggaag accaatatta agacagtag cggtaagccc ctgtactaaa   1620
agcttggctg ttttggcgga tgagagaaga ttttcagcct gatac                  1665
```

<210> SEQ ID NO 9
<211> LENGTH: 346
<212> TYPE: PRT
<213> ORGANISM: Escherichia coli
<220> FEATURE:
<221> NAME/KEY: MISC_FEATURE
<222> LOCATION: (1)..(346)
<223> OTHER INFORMATION: PBP from E coli UMEA 3200-1, has 99.4 percent
      identity to SEQ ID NO: 1

<400> SEQUENCE: 9

```
Met Lys Val Met Arg Thr Thr Val Ala Thr Val Ala Ala Thr Leu
1               5                   10                  15

Ser Met Ser Ala Phe Ser Val Phe Ala Glu Ala Ser Leu Thr Gly Ala
                20                  25                  30

Gly Ala Thr Phe Pro Ala Pro Val Tyr Ala Lys Trp Ala Asp Thr Tyr
            35                  40                  45

Gln Lys Glu Thr Gly Asn Lys Val Asn Tyr Gln Gly Ile Gly Ser Ser
        50                  55                  60

Gly Gly Val Lys Gln Ile Ile Ala Asn Thr Val Asp Phe Gly Ala Ser
65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
            100                 105                 110

Leu Lys Ser Gly Glu Leu Val Leu Asp Gly Lys Thr Leu Gly Asp Ile
        115                 120                 125

Tyr Leu Gly Lys Ile Lys Lys Trp Asp Asp Glu Ala Ile Thr Lys Leu
    130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
            180                 185                 190
```

```
Trp Pro Ile Gly Leu Gly Gly Lys Gly Asn Asp Gly Ile Ala Ala Phe
            195                 200                 205

Val Gln Arg Leu Pro Gly Ala Ile Gly Tyr Val Glu Tyr Ala Tyr Ala
    210                 215                 220

Lys Gln Asn Asn Leu Ala Tyr Thr Lys Leu Ile Ser Ala Asp Gly Lys
225                 230                 235                 240

Pro Val Leu Pro Thr Glu Glu Asn Phe Ala Asn Ala Ala Lys Gly Ala
                245                 250                 255

Asp Trp Ser Lys Thr Phe Ala Gln Asp Leu Thr Asn Gln Lys Gly Glu
                260                 265                 270

Asp Ala Trp Pro Ile Thr Ser Thr Thr Phe Ile Leu Ile His Lys Asp
            275                 280                 285

Gln Lys Lys Pro Glu Gln Gly Thr Glu Val Leu Lys Phe Phe Asp Trp
        290                 295                 300

Ala Tyr Lys Thr Gly Ala Lys Gln Ala Asn Asp Leu Asp Tyr Ala Ser
305                 310                 315                 320

Leu Pro Asp Ser Val Glu Gln Val Arg Ala Ala Trp Lys Thr Asn
                325                 330                 335

Ile Lys Asp Ser Ser Gly Lys Pro Leu Tyr
                340                 345

<210> SEQ ID NO 10
<211> LENGTH: 346
<212> TYPE: PRT
<213> ORGANISM: Shigella boydii
<220> FEATURE:
<221> NAME/KEY: MISC_FEATURE
<222> LOCATION: (1)..(346)
<223> OTHER INFORMATION: PBP from Shigella boydii ATCC 9905, has 99.7
      percent identity to SEQ ID NO: 1

<400> SEQUENCE: 10

Met Lys Val Met Arg Thr Thr Val Ala Thr Val Ala Ala Thr Leu
1               5                   10                  15

Ser Met Ser Ala Phe Ser Val Phe Ala Glu Ala Ser Leu Thr Gly Ala
                20                  25                  30

Gly Ala Thr Phe Pro Ala Pro Val Tyr Ala Lys Trp Ala Asp Thr Tyr
            35                  40                  45

Gln Lys Glu Thr Gly Asn Lys Val Asn Tyr Gln Gly Ile Gly Ser Ser
        50                  55                  60

Gly Gly Val Lys Gln Ile Ile Ala Asn Thr Val Asp Phe Gly Ala Ser
65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
                100                 105                 110

Leu Lys Ser Gly Glu Leu Val Leu Asp Gly Lys Thr Leu Gly Asp Ile
            115                 120                 125

Tyr Leu Gly Lys Ile Lys Lys Trp Asp Asp Glu Ala Ile Ala Lys Leu
    130                 135                 140

Asn Pro Gly Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Gly Trp Lys Asn Asn Val Gly Thr Gly Ser Thr Val Lys
            180                 185                 190
```

-continued

```
Trp Pro Ile Gly Leu Gly Gly Lys Gly Asn Asp Gly Ile Ala Ala Phe
            195                 200                 205

Val Gln Arg Leu Pro Gly Ala Ile Gly Tyr Val Glu Tyr Ala Tyr Ala
210                 215                 220

Lys Gln Asn Asn Leu Ala Tyr Thr Lys Leu Ile Ser Ala Asp Gly Lys
225                 230                 235                 240

Pro Val Ser Pro Thr Glu Glu Asn Phe Ala Asn Ala Ala Lys Gly Ala
                245                 250                 255

Asp Trp Ser Lys Thr Phe Ala Gln Asp Leu Thr Asn Gln Lys Gly Glu
                260                 265                 270

Asp Ala Trp Pro Ile Thr Ser Thr Thr Phe Ile Leu Ile His Lys Asp
                275                 280                 285

Gln Lys Lys Pro Glu Gln Gly Thr Glu Val Leu Lys Phe Phe Asp Trp
            290                 295                 300

Ala Tyr Lys Thr Gly Ala Lys Gln Ala Asn Asp Leu Asp Tyr Ala Ser
305                 310                 315                 320

Leu Pro Asp Ser Val Val Glu Gln Val Arg Ala Ala Trp Lys Thr Asn
                325                 330                 335

Ile Lys Asp Ser Ser Gly Lys Pro Leu Tyr
            340                 345
```

<210> SEQ ID NO 11
<211> LENGTH: 346
<212> TYPE: PRT
<213> ORGANISM: Trichuris trichiura
<220> FEATURE:
<221> NAME/KEY: MISC_FEATURE
<222> LOCATION: (1)..(346)
<223> OTHER INFORMATION: PBP from Trichuris trichiura , has 98.8 percent
      identity to SEQ ID NO: 1

<400> SEQUENCE: 11

```
Met Lys Val Met Arg Thr Thr Val Ala Thr Val Ala Ala Thr Leu
1               5                   10                  15

Ser Met Ser Ala Phe Ser Val Phe Ala Glu Ala Ser Leu Thr Gly Ala
                20                  25                  30

Gly Ala Thr Phe Pro Ala Pro Val Tyr Ala Lys Trp Ala Asp Thr Tyr
            35                  40                  45

Gln Lys Glu Thr Gly Asn Lys Val Asn Tyr Gln Gly Ile Gly Ser Ser
        50                  55                  60

Gly Gly Val Lys Gln Ile Ile Ala Asn Thr Val Asp Phe Gly Ala Ser
65                  70                  75                  80

Asp Ala Pro Leu Ser Asp Glu Lys Leu Ala Gln Glu Gly Leu Phe Gln
                85                  90                  95

Phe Pro Thr Val Ile Gly Gly Val Val Leu Ala Val Asn Ile Pro Gly
            100                 105                 110

Leu Lys Ser Gly Glu Leu Val Leu Asp Gly Lys Thr Leu Gly Asp Ile
        115                 120                 125

Tyr Leu Gly Lys Ile Lys Lys Trp Asp Asp Glu Ala Ile Ala Lys Leu
130                 135                 140

Asn Pro Asp Leu Lys Leu Pro Ser Gln Asn Ile Ala Val Val Arg Arg
145                 150                 155                 160

Ala Asp Gly Ser Gly Thr Ser Phe Val Phe Thr Ser Tyr Leu Ala Lys
                165                 170                 175

Val Asn Glu Glu Trp Lys Asn Asn Val Gly Thr Gly Ser Thr Val Lys
            180                 185                 190
```

```
Trp Pro Ile Gly Leu Gly Gly Lys Gly Asn Asp Gly Ile Ala Ala Phe
        195             200             205
Val Gln Arg Leu Pro Gly Ala Ile Gly Tyr Val Glu Tyr Ala Tyr Ala
        210             215             220
Lys Gln Asn Asn Leu Ala Tyr Thr Lys Leu Ile Ser Ala Asp Gly Lys
225             230             235             240
Pro Val Leu Pro Thr Glu Glu Asn Phe Ala Asn Ala Ala Lys Gly Ala
            245             250             255
Asp Trp Ser Lys Thr Phe Ala Gln Asp Leu Thr Asn Gln Lys Gly Glu
            260             265             270
Asp Ala Trp Pro Ile Thr Ser Thr Thr Phe Ile Leu Val His Lys Asp
            275             280             285
Gln Lys Lys Pro Glu Gln Gly Val Glu Val Leu Lys Phe Phe Asp Trp
        290             295             300
Ala Tyr Lys Thr Gly Ala Lys Gln Ala Asn Asp Leu Asp Tyr Ala Ser
305             310             315             320
Leu Pro Asp Ser Val Val Glu Gln Val Arg Ala Ala Trp Lys Thr Asn
            325             330             335
Ile Lys Asp Ser Ser Gly Lys Pro Leu Tyr
            340             345
```